United States Patent [19]
Timasheff et al.

[11] Patent Number: 5,760,092
[45] Date of Patent: Jun. 2, 1998

[54] ALLOCOLCHINONES AND USES THEREOF

[75] Inventors: Serge M. Timasheff; Marina J. Gorbunoff, both of Wellesley; Bernardo Perez-Ramirez, Brookline, all of Mass.

[73] Assignee: Brandeis University, Waltham, Mass.

[21] Appl. No.: 615,526

[22] Filed: Mar. 11, 1996

Related U.S. Application Data

[63] Continuation-in-part of Ser. No. 527,372, Sep. 13, 1995, abandoned.
[51] Int. Cl.⁶ .......................... A01N 35/00; A61K 31/12
[52] U.S. Cl. .......................... 514/680; 514/683; 514/674; 514/685; 568/325; 568/326
[58] Field of Search .......................... 568/325, 326; 514/674, 680, 655, 683

[56] References Cited

PUBLICATIONS

Hastie, S. B., "Spectroscopic and kinetic features of allocolchicine binding to tubulin", Biochemistry, 28(19), pp. 7753–7760, 1989, see abstract, 1989.

Fitzgerald, T. J., "Molecular features of cochicine associated with antimitotic activity and inhibition of tubulin polymerization", Biochem. Pharmacol., 25(12), pp. 1383–1387, 1976, see abstract, 1976.

Andreu, J. M., et al., "Interaction of Tubulin with Bifunctional Colchicine Analogues: An Equlibrium Study," Biochemistry, 23(8):1742–1752 (1984).

Andreu, J. M., et al., "Mechanism of Colchicine Binding to Tubulin. Tolerance of Substituents in Ring C' of Biphenyl Analogues," Biochemistry, 30(15):3777–3786 (1991).

Medrano, F. J., et al., "Roles of Colchicine Rings B and C in the Binding of Process to Tubulin," Biochemistry, 28(13):5589–5599 (1989).

Capraro, H. G. and A. Brossi, "The Alkaloids," A. Brossi, editor, vol. XXIII, Academic Press, pp. 1–70 (1984).

Medrano, F. J., et al., "Roles of Ring C Oxygens in the Binding of Colchicine to Tubulin," Biochemistry, 30:3770–3777 (1991).

Andreu, J. M. and Timasheff, S. N., "Interaction of Tubulin with Single Ring Analogues of Colchicine," Biochemistry, 21:534–543 (1982).

Timasheff, S. N., et al., "Physical and Spectroscopic Methods for the Evaluation of the Interaction of Antimitotic Agents with Tubulin," Pharm. Ther., 52:191–210 (1981).

Andreu, J. M. and Timasheff, S. M., "Conformational States of Tubulin Liganded to Colchicine, Tropolone Methyl Ether and Podophyllotoxin," Biochemistry, 21:6465 (1982).

Primary Examiner—Marianne M. Cintins
Assistant Examiner—Dwayne C. Jones
Attorney, Agent, or Firm—Hamilton, Brook, Smith & Reynolds, P.C.

[57] ABSTRACT

Disclosed are allocolchinones, which are anti-mitotic agents. Allocolchinones bind to tubulin reversibly and are more effective at inhibiting microtubule formation than colchicine. 7-Acetamido-allocolchinone inhibits the growth of a number of tumor cell lines at concentrations about 100 times lower than colchicine. Also disclosed is a method of treating an individual with cancer by administering a composition which comprises a therapeutically effective amount of an allocolchinone which inhibits microtubule assembly. Administering a therapeutically effective amount of a composition which comprises an allocolchinone which inhibits microtubule assembly can also be used for treating inflammatory diseases, multiple sclerosis, primary biliary cirrhosis, Alzheimer's Disease and Behcet's Disease.

24 Claims, 1 Drawing Sheet

ALLOCOLCHINONES AND USES THEREOF

RELATED APPLICATIONS

This application is a Continuation-In-Part of U.S. Ser. No. 08/527,372, filed Sep. 13, 1995, now abandoned the teachings of which are incorporated herein by reference in their entirety.

BACKGROUND OF THE INVENTION

Colchicine (1) is an alkaloid having a tricyclic ring structure. A numbering system for the ring atoms and a lettering system for the three rings are indicated in (1).

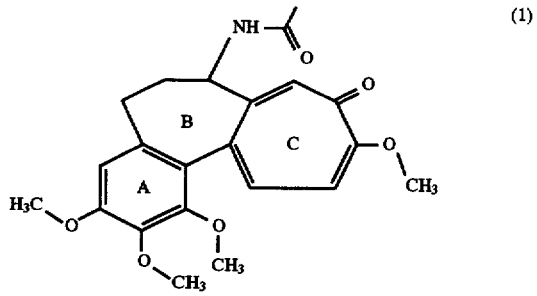

Colchicine binds to the protein tubulin irreversibly. Tubulin is part of the cellular cytoskeleton, of the mitotic apparatus, of neurons and a building block of microtubules. The binding of colchicine to tubulin interferes with microtubule-dependent cell processes. One important example of a microtubule-dependent process with which colchicine interferes is the assembly of microtubules during metaphase. Inhibition of microtubule assembly results in the inability of a cell to move its chromosomes during cell division causing the cell to arrest during metaphase and die. Consequently, colchicine acts as an anti-mitotic agent.

Many anti-cancer drugs act by causing cell death during mitosis. However, the use of colchicine as an anti-cancer drug is precluded by its high toxicity. The toxicity of colchicine is thought to be due in part to the fact that colchicine binds irreversibly to tubulin. Consequently, the treatment of cancer could be greatly advanced with new drugs that inhibit microtubule assembly by binding to tubulin but which are less toxic than colchicine.

Colchicine has long been used as an agent against inflammatory disease, such as gout and Mediterranean fever. Colchicine is also used to treat other diseases, such as multiple sclerosis, primary biliary cirrhosis, Alzheimer's Disease and Behcet's Disease. Thus, there is also a need for less toxic drugs having greater effectiveness with reduced side effects against these diseases.

SUMMARY OF THE INVENTION

The present invention is based on the discovery that allocolchinones, like colchicine, bind to tubulin. However, the binding of allocolchinones to tubulin is reversible, in contrast to colchicine. Certain allocolchinones are also more effective than colchicine in inhibiting microtubule formation in vitro. In addition, it has been found that the concentration of 7-acetamido-allocolchinone at which 50% of the cell growth is inhibited is about 100 fold lower than colchicine against most of the tumor cell lines in the National Cancer Institute's (NCI) revised anti-cancer screen (Grever et al., Seminars in Oncology 19:622 (1992), Alley et al., Cancer Research 48:589 (1988) and Montes et al., J. National Cancer Institute 83:757 (1991)). 7-Butyramido-allocolchinone is also active in the NCI screen.

One embodiment of the present invention is an inhibitor of microtubule formation comprising an allocolchinone, which comprises the tricyclic ring system of allocolchicine. An allocolchinone also has —CO—R (wherein R is a lower alkyl or substituted lower alkyl) attached to position 9 of the tricyclic ring system instead of the carbomethoxy group (—CO—OCH₃) of allocolchicine.

Other embodiments of the present invention include methods of treating an individual with cancer, inflammatory disease, multiple sclerosis, primary biliary cirrhosis, Alzheimer's Disease and Behcet's Disease. The method comprises administering to the individual a composition comprising a therapeutically effective amount of an allocolchinone which inhibits microtubule formation.

The allocolchinones of the present invention are anti-mitotics and can consequently be used as anti-cancer agents. Based on results with 7-acetamido-allocolchinone and 7-butyramido-allocolchinone in the National Cancer Institute anti-cancer screen, allocolchinones can be more effective in inhibiting the growth of cancer cells than colchicine. Because they bind reversibly to tubulin, allocolchinones are also expected to be less toxic than colchicine.

DETAILED DESCRIPTION OF THE INVENTION

Figure 1:
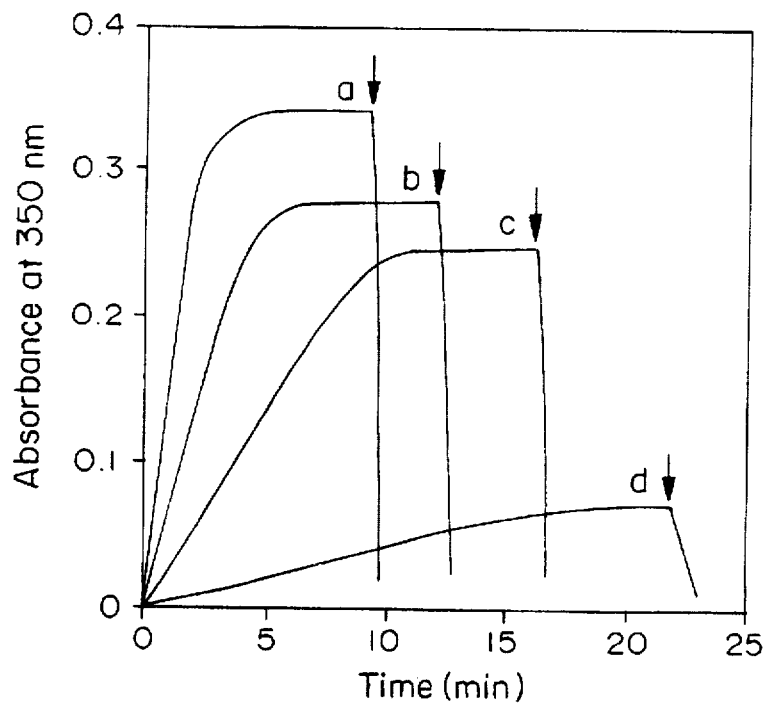
FIG. 1 is a graph of absorbance versus time showing the decrease in plateau turbidity induced by the addition of increasing amounts of 7-acetamido-allocolchinone to tubulin.

Inhibitors of microtubule assembly comprising an allocolchinone have the tricyclic ring system of allocolchicine (2). Allocolchinones differ from allocolchicine in that an alkyl ketone group (—CO—R, wherein R is a lower alkyl or substituted lower alkyl), preferably a methyl ketone group, substitutes for the carbomethoxy group (—CO—OCH₃) in the C ring of allocolchicine.

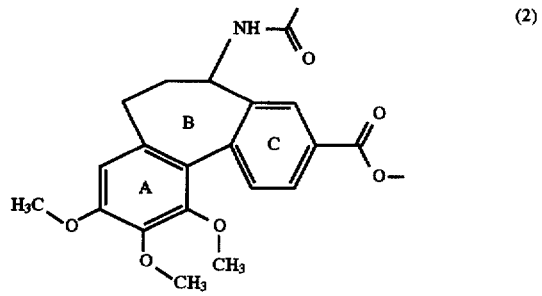

The present invention also encompasses substitutions at other positions on the A, B or C rings which result in allocolchinones that inhibit microtubule assembly. Suitable substitutions can occur at positions one, two, three and seven and include substituents which are the same as or different from those found in colchicine, known colchicine analogues or allocolchicine. Substitutions can also occur at positions which are unsubstituted in allocolchicine, e.g. positions four, five and six. In a preferred embodiment, the compounds of the present invention are represented by a structure selected from the group consisting of:

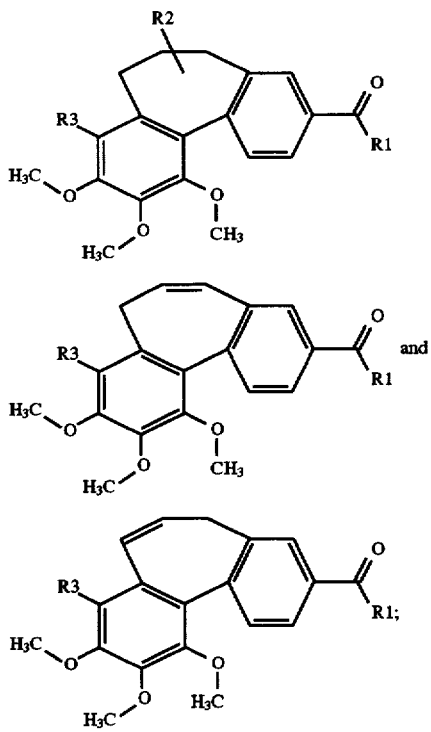

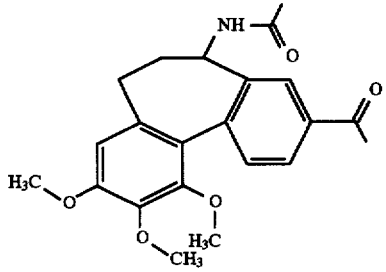

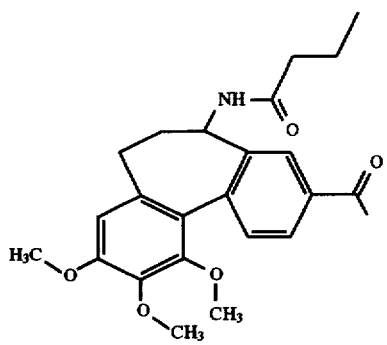

R1 is selected from the group consisting of methyl, ethyl, fluorinated methyl and fluorinated ethyl. Methyl is preferred.

R2 is selected from the group consisting of —H, =O, amino, NHR', hydroxy, —OR', thiol, —O—CO—R', —O—CO—R", —SR', —NH—CO—R', —NH—CO—R", —NH—CO—O—R', —NH—CHO, —NH—CHS, —NH—CO—CH$_2$OH, —NH—CS—R' and lower alkyl.

R3 is selected from the group consisting of —H, —OR', —CHCl$_2$, —CN, —NHCHO, —CH$_2$OH, lower alkyl, —NH—CO—R', —CH$_2$N(CH$_3$)$_2$, —COOR', and —O—CO—R'. R3 is preferably —H.

R' is a lower alkyl group. R" is a substituted lower alkyl group.

A fluorinated methyl or ethyl group can have one or more fluorine atoms. Optionally, a fluorinated methyl or ethyl group can be perfluorinated.

A lower alkyl group includes C1 to about C10 straight or branched hydrocarbons. The hydrocarbon can be saturated or can include one or more units of unsaturation. Preferred lower alkyl groups include C1 to about C5 straight chain hydrocarbons. Suitable substituents for a substituted lower alkyl include electron withdrawing substituents such as nitro, cyano and halo. Preferred substituents are —Br and —F.

In a preferred embodiment R2 is bound to the seven position of the B ring and R3 is —H. R2 is preferably —NH—CO—(lower alkyl), wherein suitable lower alkyl groups include methyl, ethyl, propyl, butyl and pentyl. It is most preferred that R1 is methyl and R2 is —NH—CO—CH$_3$ or —NH—CO—CH$_2$—CH$_2$—CH$_3$, i.e. the compound is 7-acetamido-allocolchinone (3) or 7-butryamido-allocolchinone (4).

Another embodiment of the present invention is a method of inhibiting the assembly of tubulin into microtubules. The method can be used in vivo or in vitro. The method comprises contacting tubulin with an inhibitory amount of a compound represented by a structure in Formula (I). It is preferred that R1 is methyl, R2 is —NH—CO-alkyl and is attached to the seven position of ring B, and R3 is —H. It is most preferred that the compound is 7-acetamido-allocolchinone or 7-butyramido-allocolchinone.

An "inhibitory amount" of the compound is the quantity of the compound which results in significantly less microtubule formation in the presence of the compound than in its absence. Suitable inhibitory amounts of the compound range from about $1\times10^{-7}$M to about $15\times10^{-7}$M. It is preferred that from about $1\times10^{-7}$M to about $5\times10^{-7}$M of the compound be used.

Specific examples where a compound of the present invention is being used to inhibit microtubule formation are given in Example 4. Microtubule assembly was inhibited in vitro by 7-amino-allocolchinone, 7-acetamido-allocolchinone and 7-butryamido-allocolchinone. The LC$_{50}$ for these compounds are $3\times10^{-6}$M, $3\times10^{-7}$M and $6\times10^{-7}$M, respectively.

Another embodiment of the present invention is a method of treating cancer in an individual. The method comprises administering to the individual a composition comprising a therapeutically effective amount of an allocolchinone which inhibits microbulule assembly. Examples include a compound represented by a structure in Formula I. The allocolchinones of the present invention have been found to selectively inhibit mitotic division in certain types of cancer cells. Therefore, this embodiment is also a method of inhibiting mitotic division in an individual. The method comprises administering to the individual a composition comprising an anti-mitotic amount of an allocolchinone which inhibits microtubule assembly. Examples include a compound represented by a structure in Formula I. An "anti-mitotic amount" of a compound is that quantity of the compound which results in significantly greater cell death among cells undergoing mitotic division in an individual after being administered the compound compared with before being administered the compound. It is preferred that R1 be methyl, that R2 be attached at position seven of ring B and that R3 be —H. More preferably, R2 is —NH—CO— (lower alkyl). Preferred lower alkyl groups include methyl, ethyl, propyl, butyl and pentyl. It is most preferred that the compound is 7-acetamido-allocolchinone or 7-butyramido-allocolchinone.

Types of cancer cells against which the compounds of the present invention are effective are provided in Example 5. 7-Acetamido-allocolchinone, 7-butyramido-allocolchinone and colchicine were tested in the National Cancer Institute's in vitro Disease—Oriented Primary Antitumor Screen against sixty cell tumor lines. The data in Tables I–V give the $GI_{50}$ (concentration at which cell growth is slowed 50%), the TGI (the total growth inhibition, i.e. the concentration at which the cell population does not increase) and $LC_{50}$ (the concentration at which the cell population is reduced by 50%) for 7-acetamido-allocolchinone (Tables I and III), 7-butyramido-allocolchinone (Tables IV and V) and colchicine (Table II). Against most of the cell lines tested, the $GI_{50}$ of 7-acetamido-allocolchinone was about 100 times lower than for colchinone. 7-Butyramido-allocolchinone showed activity similar to 7-acetamidoallocolchinone. Both of these compounds showed selectivity against colon cancer cell line COLO 205 (see $LC_{50}$ for COLO 205 in Tables III, IV and V).

The observation that the binding of 7-acetamido-allocolchinone to tubulin is reversible is consistent with 7-acetamido-allocolchinone being less toxic than colchicine.

Another embodiment of the present invention is a method of treating inflammatory disease in an individual, such as gout, Mediterranean fever, osteoarthritis and rheumatoid arthritis. The method comprises administering to the individual a composition comprising a therapeutically effective amount of an allocolchinone which inhibits microtubule assembly. Examples include a compound represented by a structure in Formula I. Other diseases such as multiple sclerosis, primary biliary cirrhosis, Alzheimer's Disease, Behcet's Disease can also be treated by administering a therapeutically effective amount of an allocolchinone which inhibits microtubule assembly. Examples include a compound represented by a structure in Formula I.

A "therapeutically effective amount" is the quantity of compound which results in an improved clinical outcome as a result of the treatment compared with a typical clinical outcome in the absence of the treatment. In the case of cancer, an "improved clinical outcome" includes a longer life expectancy. It can also include slowing or arresting the rate of growth of a tumor, causing a shrinkage in the size of the tumor or a decreased rate of metastasis. In the case of inflammatory disease, an "improved clinical outcome" includes less pain and inflammation as a result of the disease and improved mobility of the body parts afflicted with the disease.

The amount of compound administered to the individual will depend on the type and severity of the disease and on the characteristics of the individual, such as general health, age, sex, body weight and tolerance to drugs. The skilled artisan will be able to determine appropriate dosages depending on these and other factors. Typically, a therapeutically effective amount of the compound can range from about 1 mg per day to about 1000 mg per day for an adult. Preferably, the dosage ranges from about 1 mg per day to about 100 mg per day.

The compound can be administered orally, for example, in capsules, suspensions or tablets or by parenteral administration. Parenteral administration can include, for example, systemic administration, such as by intramuscular, intravenous, subcutaneous, or intraperitoneal injection.

The compound can be administered to the individual in conjunction with an acceptable pharmaceutical carrier as part of a pharmaceutical composition for treating cancer, inflammatory disease, or the other diseases discussed above. Suitable pharmaceutical carriers may contain inert ingredients which do not interact with the compound. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The invention will now be further and specifically described by the following examples.

EXEMPLIFICATION

EXAMPLE 1

Synthesis of 7-Acetamido-allocolchinone

Procedure

This compound was synthesized by the method of the modified synthesis of ketones by Grignard reaction with esters (I. Yorifuji and T. Kikkawa, Synthesis, 877–880, (1980)).

Tetrahydrofuran (THF), 0.03M methylmagnesium bromide (Aldrich) and 0.11M triethylamine, freshly distilled from $P_2O_5$, were mixed in a reaction flask kept under a dry $N_2$ atmosphere. The reaction flask was kept in an ice/water bath with stirring. 0.005M allocolchicine in 150 ml benzene and 5 ml THF was added during the course of 3 hours. After work up of the reaction mixture, the material obtained was chromatographed 2× on silica plates and recrystallized from ethyl acetate.

Analytical Data

M.P. 219°–220° CHN found: C 68.93; H 6.69; N 3.69 Theory: 68.89; 6.57; 3.65 U.V.: $\lambda_{max}$ 301; $\lambda$min 265 Ex Coeff.

in 1% DMSO pH 7 0.01M phosphate, $\lambda_{300}$; 15,540 $M^{-1}$ $cm^{-1}$ Mass Spec: 383 (79%); 384 (22%) 324 (77%) (loss of $CH_3CONH$) IR ($CCl_4$: 1675 (C=O ketone); 1645 (C=O amide); 1595 (aromatic); 1484 (aromatic); 1463 (aromatic); 1292 [C—(C=O)—)—C]; 1232 (C—O ether); 1106 (C—O) $cm^{-1}$.

$^1$H NMR ($CDCl_3$; δ7.98 [dd, J=1.7 Hz, 3 Hz, H—C (3')]; 7.84 [dd, J=8.0 Hz, 1.7 Hz, H—C (5')]; 7.60 [dd, J=8.0 Hz, 3.0 Hz, H—C (6')]; 6.60 [s, H—C(5)]; 6.44 (d, J-8.0 Hz, H—N); 4.91 [m, H—C (9)]; 3.94, 3.91 (s, ring A m-, p-$OCH_3$); 3.59 (s, ring A O—$OCH_3$) 2.64 (s, ring C ketone $CH_3$); 2.48 [m, H—C (7)]; 205 (s, amide $CH_3$); 1.85 [m, H—C(8)].

$^{13}$C NMR ($CDCl_3$; δ198.2 (C=O, ketone); 169.5 (C=O, amide); 153.3 (C-2); 151.2 (C-4); 140.1 (C-2'); 141.3 (C-3); 135.7 (C-4'); 134.8 (C-1'); 130.3 (C-6'); 126.9 (C-5); 123.9 (C-1, C-6); 121.9 (C-3'); 107.9 (C-5); 61.2, 60.7, 56.1 (ring A $OCH_3$); (52.5 (C-9); 39.2 (C-7); 30.4 (C-8); 26.6 (ketone $CH_3$; 23.2 (amide $CH_3$).

EXAMPLE 2

Synthesis of 7-Amino-allocolchinone

Procedure

7-Acetamido-allocolchinone from Example 1 was kept at 37° C. in 4% $H_2SO_4$ in methanol for two weeks. After work up, the material was chromatographed on silica plates to give the pure amine in 85% yield. U.V.:$\lambda_{max}$297

Analytical Data $\Sigma_{300}$=14,010 $M^{-1}$ $cm^{-1}$ in 1% DMSO
Mass Spec: 341 (100%); 324 (84%) (loss of $NH_2$)

IR ($CCl_4$): 1674 (C=O ketone); 1598 (aromatic); 1484 (aromatic); 1463 (aromatic); 1291 [C—(C=O)—C]; 1231 (C—O ether); 1101 (C—O) $cm^{-1}$.

$^1$H NMR ($CDCl_3$: δ8.27 [d,J=1.5 Hz, H—C(3')]; 8.3 (ring B $H_2N$); 7.91 [dd, J=1.7 Hz, 8.0 Hz, H—C(5')]; 7.55 [d, J=8.0 Hz; H—C(6')]; 6.52 (s, H—C(5)]; 4.60 [m, H—C(9)]; 3.92, 3.91 (s, ring A m-, p-$OCH_3$); 3.65 (s, ring A O—$CH_3$; 2.66 (s, ring C ester $CH_3$); 2.40 [m, H—C(7)]; 1.8 [m, H—C(8)].

$^{13}$C NMR ($CDCl_3$): δ198.2 (C=O); 153.2 (C-2, C-4); 150.8 (C-1'); 142.6 (C-2'); 140.9 (C-3); 135.7 (C-4'); 130.2 (C-6'); 126.2 (C-5'); 123.8 (C-1, C-6); 122.8 (C-3'); 107.5 (C-5); 61.0, 59.1, 56.0 (ring A $OCH_3$); 50.7 (C-9); 42.0 (C-7); 30.9 (C-8); 26.6 (ketone $CH_3$).

EXAMPLE 3

Synthesis of 7-Butyramido-allocolchinone

The pure amine from Example 2 was reacted with butyric acid in $CH_2Cl_2$ using 1.3 dicyclohexylcarbodiimide as catalyst. After stirring overnight, the solution was filtered and worked up. The crude product was chromatographed on silica plates and recrystallized several times from 1:1 $C_6H_6$/Hexane.

Analytical Data

U.V.: $\lambda_{max}$: 301 in 30% $CH_3OH$ $\Sigma_{300}$=13 565 $M^4$ $cm_{-1}$
Mass Spec: 411 (89%); 412 (28%); 324 (100%); (loss of $CH_3CH_2CH_2CONH$)

IR($CCl_4$): 1675 (C=O, ketone)l; 1645 (C—O amide); 1599 (aromatic); 1484 (aromatic); 1464 (aromatic); 1292 [C—(C=O)—C]; 1233 (C—O either); 1101 (C—O) $cm^{-1}$.

$^1$H NMR ($CDCl_3$): δ8.27 [d, J=1.5 Hz, H—C(3')]; 8.3 (ring B $H_2N$); 7.91 [dd, J=1.7 Hz, 8.0 Hz, H—C(5')]; 7.55 [d, J=8.0 Hz; H—C(6')]; 6.52 [s, H—C(5)]; 4.60 [m, H—C(9)]; 3.92, 3.91 (s, ring A m-, p-$OCH_3$); 3.64 [s, ring A O—$CH_3$); 2.63 (s, ring C ketone $CH_3$); 2.45 [m, H—C (7)]; 1.85 [m, H—C (11)]; 1.68 [9, H—C (12)]; 0.96 [t, J=7.3 Hz, H—C (13)].

$^{13}$C NMR ($CDCl_3$); δ198.1 (C=O, ketone); 172.4 (C=O, amide); 153.3 (C-2); 151.3 (C-4); 142.0 (C-2'); 141.4 (C-3); 134.7 (C-1'); 131.8 (C-4'); 130.4 (C-6'); 126.9 (C-5'); 124.0 (C-1); 123.9 (c-6); 122.0 (C-3'); 107.8 (C-5); 61.3, 61.2, 56.0 (ring A $OCH_3$); 52.4 (C-9); 42.0 (C-7); 39.3 (C-8); 30.4 (C-11); 26.6 (ketone $CH_3$); 19.1 (C-12); 13.8 (c-13).

In the NMR analyses, the positions have been numbered to conform to biphenyls (they deviate from the standard numbering of colchicine related compounds) as follows:

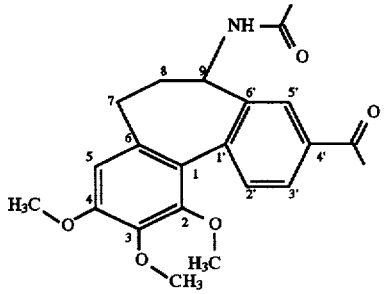
(3)

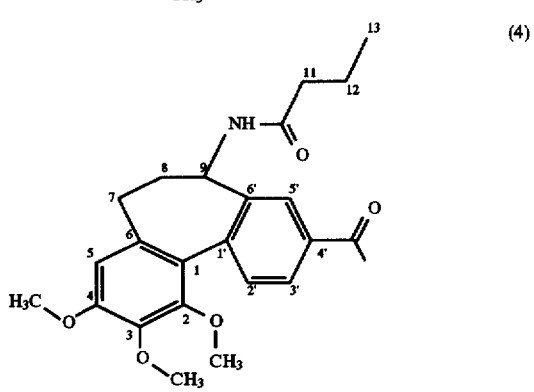
(4)

EXAMPLE 4

Microtubule Inhibition Assay

Tubulin was prepared from fresh calf brains (one hour maximum after slaughter) by a modified Weisenberg procedure (Weisenberg et al, *Biochemistry*, 7:4466 (1968)); Na and Timasheff, *Biochemistry*, 19:1347 (1980). Protein aliquots (40 mg, 40–50 mg/ml) were stored in liquid nitrogen in a buffer that consisted of 0.01M sodium phosphate, 0.1 mM GTP, 0.5 mM $MgCl_2$, 1M sucrose, pH 7.0. Prior to each assembly experiment, samples of tubulin were thawed at 20° C. and the bulk of the sucrose was removed from the tubulin solution by a Sephadex G-25 dry column procedure (Na and Timasheff, 1980). The resulting protein solution was cleared of aggregates by centrifugation at 35,000 g for 30 minutes. The final equilibration of the protein with the assembly buffer was by gel chromatography on a Sephadex G-25 column (Na and Timasheff, *Methods Enzymol.*, 85:393 (1982)). The protein was maintained on ice and used within 4 hours of sucrose removal. Tubulin concentrations were determined spectrophotometrically at 275 nm in 6M guanidine hydrochloride (Na and Timasheff, *J. Mol. Biol.*, 15:165 (1981)).

The self-assembly of tubulin was monitored turbidimetrically (Gaskin et al., *J. Mol. Biol.*, 89:737 (1974); Lee and Timasheff, *Biochemistry*, 16:1754 (1977)) at 350 nm on a Cary 118 recording spectrophotometer. It is known that the turbidity is proportional to the mass of microtubules formed. For the inhibition studies, tubulin, equilibrated with assembly buffer (0.01M sodium phosphate, 16 mM $MgCl_2$, 3.4M glycerol, 1 mM GTP, pH 7.0), was supplemented with increasing concentrations of the drug (7-acetamido-allocolchinone in this case) by addition of a concentrated stock solution of the drug in DMSO. The concentration of 7-acetamido-allocolchinone was determined by absorbance at 300 nm using 15,540 $M^{-1}$ $cm^{31\ 1}$ as the extinction coefficient. The final concentration of DMSO never exceeded 1%. The solution was then incubated at 20° C. for 30 minutes prior to assembly. The protein solution was then transferred into a thermostatted cuvette maintained at 10° C. and assembly was initiated by rapidly switching the water supply to a second water bath maintained at 37° C. The development of turbidity was monitored and recorded in the spectrophotometer chart recorder. The results are summarized in FIG. 1, which shows the decrease in plateau turbidity induced by the addition of increasing amounts of 7-acetamido-allocolchinone. Tubulin concentration was $2.1 \times 10^{-5}$M; the concentration of 7-acetamido-allocolchinone was (a) 0.0M, (b) $1.1 \times 10^{-7}$M, (c) $1.9 \times 10^{-7}$M and (d) $5.04 \times 10^{-7}$M.

Figure 2:
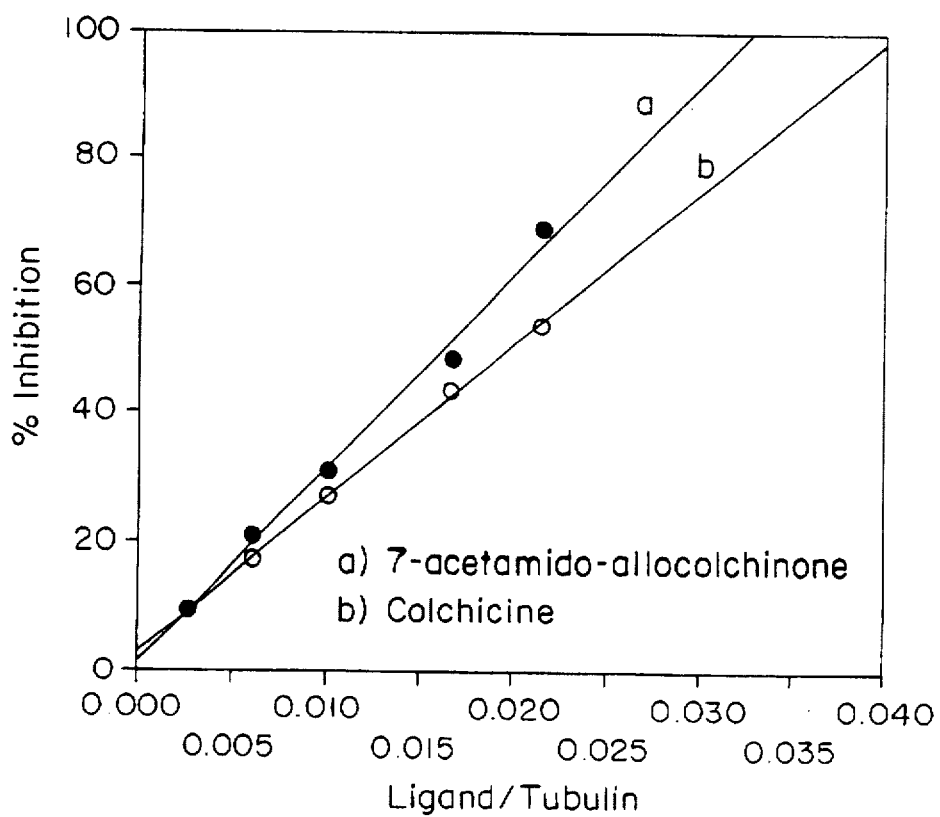
FIG. 2 is a graph of the percent inhibition of microtubule formation versus the drug (colchicine or 7-acetamido-allocolchinone) to tubulin molar concentration ratio showing the dependence of microtubule assembly inhibition on the drug to this ratio.

The turbidity plateau values relative to the turbidity generated with pure protein were then plotted against colchicine and 7-acetamido-allocolchinone concentration, expressed as moles of drug per mole of protein in the solution, as shown in FIG. 2.

It is seen that 7-acetamido-allocolchinone is more active than colchicine. At a drug to tubulin molar concentration ratio of about 0.030, 7-acetamido-allocolchinone is about 20% more active than colchicine.

EXAMPLE 5

Inhibition of Tumor Cell Growth by 7-Acetamido-Allocolchinone

7-Acetamido-allocolchinone and colchicine were tested in the National Cancer Institute's in vitro disease-oriented primary antitumor screen, according to published procedures (Grever et al., *Seminars in Oncology* 19:622 (1992), Alley et al., *Cancer Research* 48:589 (1988) and Montes et al., *J. National Cancer Institute* 83:757 (1991)). The effect of the test compound on the cell line was measured by calculating the percentage growth (PG) of the cell line in the presence of the test compound. This was calculated according to one or the other of the following equations:

If (Mean $OD_{test}$–Mean $OD_{zero}$)$\geq 0$, then PG=100×(Mean $OD_{test}$–Mean $OD_{zero}$)/(Mean $OD_{ctl}$–Mean $OD_{zero}$)

If (Mean $OD_{test}$–Mean $OD_{zero}$)<0, then PG=100×(Mean $OD_{test}$–Mean $OD_{zero}$)/Mean $OD_{zero}$ where Mean $OD_{zero}$ = The average of optical density measurements of SRB-derived color just before exposure of cells to the test compound.

Mean $OD_{test}$ = The average of optical density measurements of SRB-density color after 48 hours exposure of cells to the test compound.

Mean $OD_{ctl}$ = The average of optical density measurements of SRB-derived color after 48 hours with no exposure of cells to the test compound.

The results for colchicine, 7-butyramido-allocolchinone and 7-acetamido-allocolchinone against each cell line tested are given below in Tables I–V. The first two columns describe the subpanel (e.g., leukemia) and cell line (e.g., CCRF-CEM) involved. The next two columns list the Mean $OD_{zero}$ and Mean $OD_{ctl}$; the next five columns list the Mean $OD_{test}$ for each of five different concentrations. Each concentration is expressed as the $\log_{10}$ (molar or µg/ml). The next five columns list the calculated PGs for each concentration. The response parameters $GI_{50}$, TGI and $LC_{50}$ are interpolated values representing the concentrations at which the PG is +50.0 and −50.0, respectively. Sometimes these response parameters could not be obtained by interpolation. If, for instance, all of the PGs in a given row exceeded +50, then none of the three parameters were obtainable by interpolation. In such a case, the value given for each response parameter is the highest concentration tested and is preceded by a ">" sign. This practice is extended similarly to the other possible situations where a response parameter cannot be obtained by interpolation.

Tables I, IV and V presents the results of an initial screening of 7-acetamido-allocolchinone and 7-butyramido-allocolchinone. As can be seen, it was not possible to determine most of the $GI_{50}$s, TGIs and $LC_{50}$s at the concentrations of compound tested.

The $GI_{50}$s for 7-butyramido-allocolchinone for nearly all of the cell lines tested were less than $10^{-8}$M. Tables II and III present the results of screenings of colchicine and 7-acetamido-allocolchinone, respectively, at concentrations appropriate for determining $GI_{50}$s and TGIs for each compound against most of the cell lines tested. The $GI_{50}$s for 7-acetamido-allocolchinone are about two orders of magnitude lower than for colchine for nearly all cell lines tested.

It can also be seen from the $LC_{50}$ in Tables I and IV–V that both 7-acetamido-allocolchinone and 7-butyramido-allocolchinone are selective against colon cancer cell line COLO 205.

TABLE I

| 7-Acetamido-Allocolchinone in the NCI Anti-Cancer Screen | | | | | | | |
|---|---|---|---|---|---|---|---|
| | Time | | Log10 Concentration Mean Optical Densities | | | | |
| Panel/Cell Line | Zero | Ctrl | −8.0 | −7.0 | −6.0 | −5.0 | −4.0 |
| Leukemia | | | | | | | |
| CCRF-CEM | 0.564 | 1.525 | 0.652 | 0.606 | 0.573 | 0.601 | 0.460 |
| HL-60 (TB) | 0.322 | 1.629 | 0.343 | 0.405 | 0.366 | 0.424 | 0.437 |
| K-562 | 0.293 | 1.845 | 0.386 | 0.363 | 0.358 | 0.335 | 0.326 |
| MOLT-4 | 0.548 | 1.049 | 1.056 | 0.686 | 0.666 | 0.623 | 0.503 |
| RPMI-8226 | 0.322 | 1.239 | 0.632 | 0.516 | 0.536 | 0.496 | 0.531 |
| SR | 0.300 | 1.976 | 0.743 | 0.627 | 0.562 | 0.613 | 0.654 |

TABLE I-continued

7-Acetamido-Allocolchinone in the NCI Anti-Cancer Screen

| Non-Small Cell Lung Cancer | | | | | | | |
|---|---|---|---|---|---|---|---|
| A549/ATCC | 0.534 | 1.156 | 1.109 | 1.301 | 0.957 | 0.965 | 0.930 |
| EKVX | 1.891 | 2.939 | 3.104 | 3.199 | 3.427 | 3.419 | 2.337 |
| HOP-62 | 0.361 | 1.207 | 0.746 | 0.610 | 0.622 | 0.534 | 0.546 |
| HOP-92 | 0.666 | 1.470 | 1.205 | 1.043 | 1.105 | 1.100 | 1.137 |
| NCI-H226 | 0.765 | 1.751 | 1.246 | 0.903 | 0.892 | 0.930 | 0.940 |
| NCI-H23 | 0.445 | 1.169 | 0.706 | 0.656 | 0.624 | 0.606 | 0.556 |
| NCI-H322M | 0.451 | 0.968 | 0.563 | 0.619 | 0.615 | 0.650 | 0.592 |
| NCI-H460 | 0.235 | 1.758 | 1.152 | 0.255 | 0.247 | 0.266 | 0.242 |
| NCI-H522 | 0.446 | 1.527 | 0.623 | 0.448 | 0.460 | 0.412 | 0.426 |
| Colon Cancer | | | | | | | |
| COLO 205 | 0.195 | 1.677 | 1.008 | 0.350 | 0.212 | 0.199 | 0.234 |
| HCC-2998 | 0.306 | 1.010 | 0.882 | 0.491 | 0.506 | 0.516 | 0.516 |
| HCT-116 | 0.125 | 1.256 | 0.268 | 0.211 | 0.203 | 0.194 | 0.171 |
| HCT-15 | 0.378 | 2.023 | 1.203 | 0.524 | 0.461 | 0.471 | 0.460 |
| HT29 | 0.268 | 1.581 | 0.175 | 0.150 | 0.134 | 0.149 | 0.147 |
| KM12 | 0.164 | 0.676 | 0.156 | 0.084 | 0.116 | 0.131 | 0.155 |
| SW-620 | 0.303 | 1.587 | 0.639 | 0.596 | 0.599 | 0.516 | 0.600 |
| CNS Cancer | | | | | | | |
| SF-268 | 0.753 | 2.033 | 1.646 | 1.331 | 1.237 | 1.227 | 1.161 |
| SF-295 | 0.570 | 1.971 | 0.636 | 0.478 | 0.528 | 0.512 | 0.486 |
| SF-539 | 0.794 | 1.915 | 0.664 | 0.600 | 0.607 | 0.549 | 0.560 |
| SNB-19 | 0.314 | 1.074 | 0.433 | 0.353 | 0.357 | 0.364 | 0.362 |
| SNB-75 | 0.377 | 0.962 | 0.637 | 0.672 | 0.630 | 0.627 | 0.607 |
| U251 | 0.246 | 1.184 | 0.323 | 0.279 | 0.254 | 0.276 | 0.284 |
| Melanoma | | | | | | | |
| LOX IMVI | 0.329 | 2.062 | 1.116 | 0.522 | 0.831 | 0.784 | 0.757 |
| MALME-3M | 0.595 | 1.573 | 0.954 | 0.955 | 1.049 | 1.043 | 1.010 |
| M14 | 0.241 | 0.942 | 0.345 | 0.350 | 0.395 | 0.409 | 0.324 |
| SK-MEL-2 | 0.407 | 0.741 | 0.505 | 0.475 | 0.501 | 0.492 | 0.495 |
| SK-MEL-28 | 0.390 | 1.053 | 0.753 | 0.725 | 0.787 | 0.692 | 0.722 |
| SK-MEL-5 | 0.377 | 1.423 | 0.627 | 0.404 | 0.377 | 0.366 | 0.302 |
| UACC-257 | 1.000 | 2.215 | 1.551 | 1.406 | 1.429 | 1.447 | 1.305 |
| UACC-62 | 0.451 | 1.382 | 0.746 | 0.761 | 0.747 | 0.739 | 0.762 |
| Ovarian Cancer | | | | | | | |
| IGR-OVI | 0.485 | 1.454 | 0.939 | 0.576 | 0.458 | 0.475 | 0.533 |
| OVCAR-3 | 0.488 | 1.787 | 0.739 | 0.689 | 0.753 | 0.591 | 0.557 |
| OVCAR-4 | 0.323 | 0.921 | 0.663 | 0.573 | 0.542 | 0.564 | 0.535 |
| OVCAR-5 | 0.246 | 0.525 | 0.426 | 0.375 | 0.360 | 0.379 | 0.369 |
| OVCAR-6 | 0.549 | 2.016 | 0.826 | 0.362 | 0.382 | 0.388 | 0.301 |
| SK-OV-3 | 0.423 | 1.069 | 0.729 | 0.517 | 0.485 | 0.540 | 0.484 |
| Renal Cancer | | | | | | | |
| 786-0 | 0.323 | 1.591 | 1.228 | 0.593 | 0.563 | 0.507 | 0.456 |
| A495 | 1.041 | 1.763 | 1.771 | 1.415 | 1.220 | 1.063 | 1.046 |
| ACHN | 0.468 | 1.814 | 1.096 | 0.797 | 0.822 | 0.813 | 0.741 |
| CAKI-1 | 0.483 | 1.935 | 1.537 | 0.993 | 1.012 | 1.043 | 1.015 |
| SN12C | 0.553 | 1.736 | 1.090 | 0.753 | 0.759 | 0.756 | 0.754 |
| TK-10 | 0.849 | 1.152 | 0.951 | 1.015 | 0.771 | 1.126 | 1.096 |
| UO-31 | 0.525 | 1.289 | 1.206 | 0.823 | 0.719 | 0.740 | 0.743 |
| Prostate Cancer | | | | | | | |
| PC-3 | 0.405 | 1.613 | 0.892 | 0.771 | 0.766 | 0.717 | 0.725 |
| DU-145 | 0.192 | 0.815 | 0.436 | 0.336 | 0.358 | 0.331 | 0.326 |
| Breast Cancer | | | | | | | |
| MCF7 | 0.240 | 1.301 | 0.341 | 0.346 | 0.343 | 0.337 | 0.402 |
| MCF7/ADR-RES | 0.485 | 1.550 | 1.258 | 0.594 | 0.503 | 0.479 | 0.483 |
| MDA-MB-231/ATCC | 0.209 | 0.689 | 0.417 | 0.291 | 0.257 | 0.274 | 0.363 |
| HS 578T | 0.613 | 1.592 | 0.852 | 0.951 | 0.857 | 0.877 | 0.773 |
| MDA-MB-435 | 0.403 | 1.813 | 0.119 | 0.238 | 0.194 | 0.234 | 0.262 |
| MDA-N | 0.270 | 1.546 | 0.211 | 0.290 | 0.292 | 0.264 | 0.252 |
| BT-549 | 0.535 | 0.960 | 0.850 | 0.783 | 0.899 | 0.770 | 0.761 |
| T-47D | 0.593 | 2.105 | 1.304 | 1.819 | 1.683 | 1.645 | 1.684 |

TABLE I-continued

7-Acetamido-Allocolchinone in the NCI Anti-Cancer Screen

| Panel/Cell Line | Log10 Concentration Percent Growth | | | | | GI50 | TGI | LC50 |
|---|---|---|---|---|---|---|---|---|
| | −8.0 | −7.0 | −6.0 | −5.0 | −4.0 | | | |
| Leukemia | | | | | | | | |
| CCRF-CEM | 9 | 3 | 1 | 3 | −15 | <1.00E-08 | >1.46E-05 | >1.00E-04 |
| HL-60 (TB) | 2 | 7 | 4 | 9 | 10 | <1.00E-08 | >1.00E-04 | >1.00E-04 |
| K-562 | 6 | 4 | 4 | 3 | 1 | <1.00E-08 | >1.00E-04 | >1.00E-04 |
| MOLT-4 | 34 | 9 | 5 | 5 | −5 | <1.00E-08 | 3.38E-05 | >1.00E-04 |
| RPMI-8226 | 34 | 32 | 24 | 20 | 24 | <1.00E-08 | >1.00E-04 | >1.00E-04 |
| SR | 26 | 19 | 16 | 19 | 11 | <1.00E-08 | >1.00E-04 | >1.00E-04 |
| Non-Small Cell Lung Cancer | | | | | | | | |
| A549/ATCC | 97 | 47 | 28 | 27 | 24 | 8.81E-08 | >1.00E-04 | >1.00E-04 |
| EKVX | 116 | 125 | 50 | 50 | 43 | 1.12E-05 | >1.00E-04 | >1.00E-04 |
| HOP-62 | 45 | 29 | 31 | 20 | 22 | <1.00E-08 | >1.00E-04 | >1.00E-04 |
| HOP-92 | 66 | 45 | 53 | 53 | 57 | | >1.00E-04 | >1.00E-04 |
| NCI-H226 | 45 | 12 | 11 | 15 | 16 | <1.00E-08 | >1.00E-04 | >1.00E-04 |
| NCI-H23 | 36 | 29 | 25 | 22 | 16 | <1.00E-08 | >1.00E-04 | >1.00E-04 |
| NCI-H322M | 22 | 32 | 32 | 38 | 27 | <1.00E-08 | >1.00E-04 | >1.00E-04 |
| NCI-H460 | 62 | 1 | 1 | 2 | 0 | 1.59E-08 | >1.00E-04 | >1.00E-04 |
| NCI-H522 | 16 | 0 | 1 | −8 | −5 | <1.00E-08 | 1.36E-06 | >1.00E-04 |
| Colon Cancer | | | | | | | | |
| COLO 205 | 55 | 10 | 1 | 0 | 3 | 1.29E-06 | >1.00E-04 | >1.00E-04 |
| HCC-2998 | 82 | 26 | 28 | 30 | 30 | 3.73E-08 | >1.00E-04 | >1.00E-04 |
| HCT-116 | 12 | 7 | 6 | 6 | 4 | <1.00E-08 | >1.00E-04 | >1.00E-04 |
| HCT-15 | 50 | 9 | 5 | 6 | 6 | 1.01E-08 | >1.00E-04 | >1.00E-04 |
| HT29 | −35 | −44 | −50 | −44 | −45 | <1.00E-08 | <1.00E-08 | >1.00E-04 |
| KM12 | −5 | −45 | −30 | −20 | −5 | <1.00E-08 | <1.00E-08 | >1.00E-04 |
| SW-620 | 26 | 23 | 23 | 17 | 23 | <1.00E-08 | >1.00E-04 | >1.00E-04 |
| CNS Cancer | | | | | | | | |
| SF-268 | 70 | 45 | 38 | 37 | 32 | 6.37E-06 | >1.00E-04 | >1.00E-04 |
| SF-295 | 6 | −16 | −7 | −10 | −14 | <1.00E-08 | 1.90E-08 | >1.00E-04 |
| SF-539 | −16 | −24 | −24 | −31 | −27 | <1.00E-08 | <1.00E-08 | >1.00E-04 |
| SMB-19 | 16 | 5 | 6 | 7 | 6 | <1.00E-08 | >1.00E-04 | >1.00E-04 |
| SMB-75 | 44 | 50 | 43 | 43 | 39 | | >1.00E-04 | >1.00E-04 |
| U251 | 8 | 4 | 4 | 3 | 4 | <1.00E-08 | >1.00E-04 | >1.00E-04 |
| Melanoma | | | | | | | | |
| LOX IMVI | 45 | 25 | 29 | 26 | 25 | <1.00E-08 | >1.00E-04 | >1.00E-04 |
| MALME-3M | 40 | 37 | 46 | 46 | 42 | <1.00E-08 | >1.00E-04 | >1.00E-04 |
| M14 | 15 | 16 | 22 | 24 | 12 | <1.00E-08 | >1.00E-04 | >1.00E-04 |
| SK-MEL-2 | 29 | 20 | 28 | 26 | 27 | <1.00E-08 | >1.00E-04 | >1.00E-04 |
| SK-MEL-28 | 55 | 51 | 60 | 46 | 50 | | >1.00E-04 | >1.00E-04 |
| SK-MEL-5 | 24 | 3 | 0 | −2 | −20 | <1.00E-08 | 8.86E-07 | >1.00E-04 |
| UACC-257 | 45 | 33 | 35 | 37 | 25 | <1.00E-08 | >1.00E-04 | >1.00E-04 |
| UACC-62 | 32 | 33 | 32 | 31 | 33 | <1.00E-08 | >1.00E-04 | >1.00E-04 |
| Ovarian Cancer | | | | | | | | |
| IGR-OV1 | 47 | 9 | 0 | −2 | 5 | <1.00E-08 | | >1.00E-04 |
| OVCAR-3 | 23 | 15 | 20 | 5 | 5 | <1.00E-08 | >1.00E-04 | >1.00E-04 |
| OVCAR-4 | 57 | 42 | 37 | 40 | 35 | 2.84E-08 | >1.00E-04 | >1.00E-04 |
| OVCAR-5 | 31 | 22 | 23 | 23 | 21 | <1.00E-08 | >1.00E-04 | >1.00E-04 |
| OVCAR-6 | 19 | −34 | −30 | −29 | −45 | <1.00E-08 | 2.27E-08 | >1.00E-04 |
| SK-OV-3 | | 14 | 10 | 15 | 9 | | >1.00E-04 | >1.00E-04 |
| Renal Cancer | | | | | | | | |
| 786-0 | 71 | 21 | 20 | 15 | 10 | 2.67E-08 | >1.00E-04 | >1.00E-04 |
| A495 | 101 | 52 | 25 | 3 | 1 | 1.17E-07 | >1.00E-04 | >1.00E-04 |
| ACHN | 47 | 24 | 26 | 26 | 20 | <1.00E-08 | >1.00E-04 | >1.00E-04 |
| CAKI-1 | 73 | 35 | 36 | 39 | 37 | 4.01-08 | >1.00E-04 | >1.00E-04 |
| SN12C | 45 | 17 | 17 | 17 | 17 | <1.00E-08 | >1.00E-04 | >1.00E-04 |
| TK-10 | 44 | 55 | −9 | 91 | 82 | | | >1.00E-04 |
| UO-31 | 89 | 39 | 25 | 26 | 29 | 6.04E-06 | >1.00E-04 | >1.00E-04 |
| Prostate Cancer | | | | | | | | |
| PC-3 | 40 | 30 | 30 | 26 | 26 | <1.00E-08 | >1.00E-04 | >1.00E-04 |
| DU-145 | 39 | 23 | 27 | 22 | 22 | <1.00E-08 | >1.00E-04 | >1.00E-04 |
| Breast Cancer | | | | | | | | |
| MCF7 | 10 | 10 | 10 | 9 | 15 | <1.00E-08 | >1.00E-04 | >1.00E-04 |
| CF7/ADR-RES | 73 | 10 | 2 | −1 | −1 | 2.30E-08 | 3.67E-06 | >1.00E-04 |

TABLE I-continued

7-Acetamido-Allocolchinone in the NCI Anti-Cancer Screen

| | | | | | | | | |
|---|---|---|---|---|---|---|---|---|
| MDA-MB-231/ATCC | 43 | 17 | 10 | 14 | 32 | <1.00E-08 | >1.00E-04 | >1.00E-04 |
| HS 578T | 24 | 38 | 25 | 27 | 16 | <1.00E-08 | >1.00E-04 | >1.00E-04 |
| MDA-MB-435 | −70 | −41 | −52 | −42 | −35 | <1.00E-08 | <1.00E-08 | |
| MDA-N | −22 | 2 | 2 | −2 | 1 | <1.00E-08 | | >1.00E-04 |
| BT-549 | 74 | 56 | | 55 | 56 | >1.00E-04 | >1.00E-04 | >1.00E-04 |
| T-47D | 47 | 81 | 72 | 70 | 72 | | >1.00E-04 | >1.00E-04 |

TABLE II

Colchicine in the NCI Anti-Cancer Screen

| | Time | | Log10 Concentration Mean Optical Densities | | | | |
|---|---|---|---|---|---|---|---|
| Panel/Cell Line | Zero | Ctrl | −8.0 | −7.0 | −6.0 | −5.0 | −4.0 |
| Leukemia | | | | | | | |
| CCRF-CEM | 0.364 | 1.204 | 0.851 | 0.426 | 0.377 | 0.390 | 0.397 |
| HL-60 (TB) | 0.367 | 1.476 | 0.999 | 0.347 | 0.286 | 0.280 | 0.322 |
| K-562 | 0.233 | 1.536 | 1.000 | 0.446 | 0.409 | 0.380 | 0.308 |
| MOLT-4 | 0.507 | 1.737 | 1.708 | 0.645 | 0.517 | 0.506 | 0.522 |
| RPMI-8226 | 0.651 | 1.950 | 1.161 | 0.801 | 0.780 | 0.783 | 0.855 |
| SR | 0.464 | 1.876 | 1.745 | 0.628 | 0.563 | 0.552 | 0.668 |
| Non-Small Cell Lung Cancer | | | | | | | |
| A549/ATCC | 0.266 | 1.227 | 1.234 | 0.806 | 0.663 | 0.631 | 0.374 |
| EKVX | 0.565 | 1.421 | 1.432 | 1.242 | 1.198 | 1.134 | 1.210 |
| NCI-H226 | 1.032 | 1.648 | 1.593 | 1.007 | 0.956 | 1.072 | 0.680 |
| NCI-H23 | 0.319 | 1.113 | 1.031 | 0.342 | 0.350 | 0.336 | 0.425 |
| NCI-H322M | 0.393 | 0.799 | 0.807 | 0.539 | 0.519 | 0.496 | 0.483 |
| NCI-H460 | 0.273 | 1.581 | 1.490 | 0.189 | 0.143 | 0.160 | 0.233 |
| NCI-H522 | 0.641 | 1.689 | 1.316 | 0.483 | 0.611 | 0.588 | 0.462 |
| Colon Cancer | | | | | | | |
| COLO 205 | 0.336 | 1.821 | 1.164 | 0.674 | 0.382 | 0.384 | 0.066 |
| HCC-2998 | 0.459 | 1.359 | 1.311 | 0.487 | 0.561 | 0.529 | 0.393 |
| HCT-116 | 0.075 | 0.539 | 0.427 | 0.194 | 0.221 | 0.230 | 0.075 |
| HCT-15 | 0.450 | 1.689 | 1.734 | 1.339 | 0.497 | 0.339 | 0.309 |
| HT29 | 0.230 | 1.461 | 1.350 | 0.231 | 0.227 | 0.229 | 0.199 |
| KM12 | 0.239 | 0.952 | 0.763 | 0.406 | 0.529 | 0.425 | 0.310 |
| SW-620 | 0.234 | 1.136 | 0.845 | 0.370 | 0.331 | 0.384 | 0.163 |
| CNS Cancer | | | | | | | |
| SF-268 | 0.365 | 1.259 | 1.219 | 0.854 | 0.861 | 0.789 | 0.708 |
| SF-539 | 0.400 | 1.326 | 1.107 | 0.574 | 0.552 | 0.503 | 0.613 |
| SNB-19 | 0.588 | 1.182 | 1.124 | 0.707 | 0.743 | 0.763 | 0.475 |
| SNB-75 | 0.679 | 1.594 | 1.419 | 1.206 | 1.133 | 0.997 | 0.738 |
| U251 | 0.167 | 0.750 | 0.651 | 0.239 | 0.249 | 0.226 | 0.205 |
| Melanoma | | | | | | | |
| LOX IMVI | 0.189 | 0.835 | 0.633 | 0.214 | 0.150 | 0.176 | 0.016 |
| MALME-3M | 0.501 | 1.217 | 0.891 | 0.774 | 0.817 | 0.802 | 0.353 |
| M14 | 0.393 | 1.286 | 1.035 | 0.771 | 0.732 | 0.762 | 0.197 |
| SK-MEL-2 | 0.597 | 0.900 | 0.518 | 0.449 | 0.540 | 0.504 | 0.404 |
| SK-MEL-28 | 0.253 | 1.025 | 0.786 | 0.690 | 0.669 | 0.631 | 0.356 |
| SK-MEL-5 | 0.361 | 2.334 | 1.285 | 0.537 | 0.544 | 0.509 | 0.359 |
| UACC-157 | 0.515 | 1.025 | 1.717 | 1.673 | 1.747 | 1.744 | 1.506 |
| UACC-62 | 0.799 | 1.509 | 1.507 | 1.030 | 1.003 | 1.016 | 0.239 |
| Ovarian Cancer | | | | | | | |
| IGR-OVI | 0.698 | 1.876 | 1.883 | 1.055 | 0.970 | 0.955 | 1.006 |
| OVCAR-4 | 0.498 | 1.330 | 1.283 | 1.020 | 0.992 | 0.951 | 0.913 |
| OVCAR-5 | 0.645 | 1.205 | 1.128 | 0.898 | 0.891 | 0.888 | 0.340 |
| OVCAR-8 | 0.417 | 1.303 | 1.297 | 0.403 | 0.350 | 0.377 | 0.257 |
| Renal Cancer | | | | | | | |
| 786-0 | 0.185 | 0.910 | 0.871 | 0.507 | 0.405 | 0.424 | 0.260 |
| ACHN | 0.330 | 1.630 | 1.645 | 1.079 | 0.904 | 0.863 | 0.637 |
| RXF-393 | 0.454 | 0.638 | 0.543 | 0.467 | 0.471 | 0.477 | 0.297 |
| SN12C | 0.473 | 1.474 | 1.403 | 0.813 | 0.771 | 0.743 | 0.440 |
| TK-10 | 0.783 | 1.645 | 1.651 | 1.413 | 1.440 | 1.472 | 1.395 |
| UO-31 | 0.981 | 1.792 | 1.743 | 1.751 | 1.239 | 1.215 | 1.077 |

TABLE II-continued

Colchicine in the NCI Anti-Cancer Screen

| Prostate Cancer | | | | | | | |
|---|---|---|---|---|---|---|---|
| PC-3 | 0.588 | 1.973 | 1.566 | 0.810 | 0.662 | 0.696 | 0.672 |
| DU-145 | 0.486 | 1.555 | 1.516 | 1.169 | 1.155 | 1.009 | 0.692 |
| Breast Cancer | | | | | | | |
| MCF7 | 0.554 | 1.999 | 1.334 | 0.828 | 0.817 | 0.794 | 0.671 |
| MDA-MB-231/ATCC | 0.425 | 0.931 | 0.754 | 0.713 | 0.729 | 0.669 | 0.539 |
| MDA-MB-435 | 0.336 | 1.348 | 0.652 | 0.231 | 0.263 | 0.243 | 0.223 |
| MDA-N | 0.396 | 1.798 | 0.922 | 0.757 | 0.739 | 0.778 | 0.360 |
| BT-549 | 0.615 | 0.952 | 0.848 | 0.746 | 0.757 | 0.777 | 0.488 |
| T-47D | 0.688 | 1.512 | 1.352 | 1.423 | 1.342 | 1.360 | 1.030 |

| | Log10 Concentration Percent Growth | | | | | | | |
|---|---|---|---|---|---|---|---|---|
| Panel/Cell Line | −8.0 | −7.0 | −6.0 | −5.0 | −4.0 | GI50 | TGI | LC50 |
| Leukemia | | | | | | | | |
| CCRF-CEM | 59 | 7 | 2 | 3 | 4 | 1.50E-08 | >1.00E-04 | >1.00E-04 |
| HL-60 (TB) | 57 | −5 | −22 | −24 | −10 | 1.29E-08 | 8.22E-08 | >1.00E-04 |
| K-562 | 59 | 16 | 14 | 11 | 6 | 1.62E-08 | >1.00E-04 | >1.00E-04 |
| MOLT-4 | 98 | 11 | 1 | 0 | 1 | 3.56E-08 | | >1.00E-04 |
| RPMI-8226 | 39 | 12 | 10 | 10 | 16 | <1.00E-08 | >1.00E-04 | >1.00E-04 |
| SR | 91 | 12 | 7 | 6 | 15 | 3.27E-08 | >1.00E-04 | >1.00E-04 |
| Non-Small Cell Lung Cancer | | | | | | | | |
| A549/ATCC | 101 | 56 | 41 | 38 | 11 | 2.61E-07 | >1.00E-04 | >1.00E-04 |
| EKVX | 101 | 79 | 74 | 66 | 75 | >1.00E-04 | >1.00E-04 | >1.00E-04 |
| NCI-H226 | 91 | −3 | −7 | 7 | −34 | 2.75E-08 | | >1.00E-04 |
| NCI-H23 | 90 | 3 | 4 | 2 | 13 | 2.87E-08 | >1.00E-04 | >1.00E-04 |
| NCI-H322M | 102 | 36 | 31 | 25 | 22 | 6.11E-08 | >1.00E-04 | >1.00E-04 |
| NCI-H460 | 93 | −31 | −48 | −42 | −15 | 2.23E-08 | 5.64E-08 | >1.00E-04 |
| NCI-H522 | 64 | −25 | −5 | −8 | | 1.45E-08 | 5.29E-08 | |
| Colon Cancer | | | | | | | | |
| COLO 205 | 56 | 23 | | | −81 | 1.50E-08 | | |
| HCC-2998 | 95 | 3 | 11 | 8 | −14 | 3.07E-08 | 2.24E-05 | >1.00E-04 |
| HCT-116 | 76 | 26 | 32 | 33 | | 3.27E-08 | 1.00E-04 | >1.00E-04 |
| HCT-15 | 104 | 72 | 4 | −25 | −31 | 2.09E-07 | 1.35E-06 | >1.00E-04 |
| HT29 | 91 | 0 | −1 | 0 | −13 | 2.82E-08 | 1.14E-07 | >1.00E-04 |
| KM12 | 74 | 23 | | 26 | 10 | 2.95E-08 | >1.00E-04 | >1.00E-04 |
| SW-620 | 68 | 15 | 11 | 17 | −31 | 2.17E-08 | 2.25E-05 | >1.00E-04 |
| CNS Cancer | | | | | | | | |
| SF-268 | 96 | 55 | 56 | 47 | 38 | 4.72E-06 | >1.00E-04 | >1.00E-04 |
| SF-539 | 76 | 19 | 16 | 11 | 23 | 2.87E-08 | >1.00E-04 | >1.00E-04 |
| SNB-19 | 90 | 20 | 26 | 30 | −19 | 3.73E-08 | 4.05E-05 | >1.00E-04 |
| SNB-75 | 81 | 58 | 50 | 35 | 7 | 9.09E-07 | >1.00E-04 | >1.00E-04 |
| U251 | 83 | 12 | 14 | 10 | 6 | 2.94E-08 | 4.05E-05 | >1.00E-04 |
| Melanoma | | | | | | | | |
| LOX IMVI | 69 | 4 | −21 | −7 | −76 | 1.95E-08 | 1.44E-07 | 4.22E-05 |
| MALME-3M | 54 | 38 | 44 | 42 | −30 | 1.86E-0B | 3.86E-05 | >1.00E-04 |
| M14 | 72 | 42 | 38 | 41 | −50 | 5.48E-08 | 2.84E-05 | >1.00E-04 |
| SK-MEL-2 | −13 | −25 | −10 | −16 | −32 | <1.00E-08 | <1.00E-08 | >1.00E-04 |
| SK-MEL-28 | 69 | 57 | 54 | 49 | 13 | 6.11E-06 | >1.00E-04 | >1.00E-04 |
| SK-MEL-5 | 47 | 9 | 9 | 8 | 0 | <1.00E-08 | 8.86E-05 | >1.00E-04 |
| UACC-157 | 79 | 76 | 81 | 61 | 65 | >1.00E-08 | >1.00E-04 | >1.00E-04 |
| UACC-62 | 64 | 21 | 19 | 20 | −70 | 6.14E-04 | 1.66E-05 | 5.96E-05 |
| Ovarian Cancer | | | | | | | | |
| IGR-OV1 | 101 | 30 | 23 | 22 | 26 | 5.25E-08 | >1.00E-04 | >1.00E-04 |
| OVCAR-4 | 94 | 63 | 59 | 54 | 50 | 9.34E-05 | >1.00E-04 | >1.00E-04 |
| OVCAR-5 | 86 | 45 | 44 | 43 | −47 | 7.63E-08 | 3.01E-05 | >1.00E-04 |
| OVCAR-8 | 99 | | | | −39 | | | >1.00E-04 |
| Renal Cancer | | | | | | | | |
| 786-0 | 95 | 44 | 30 | 33 | 10 | 7.74E-08 | >1.00E-04 | >1.00E-04 |
| ACHN | 101 | 58 | 44 | 41 | 24 | 3.69E-07 | >1.00E-04 | >1.00E-04 |
| RXF-393 | 48 | 7 | 9 | 13 | | <1.00-08 | | |
| SN12C | 93 | 34 | 30 | 27 | −7 | 5.34E-08 | 6.19E-05 | >1.00E-04 |
| TK-10 | 101 | 73 | 76 | 80 | 71 | >1.00E-04 | >1.00E-04 | >1.00E-04 |
| UO-31 | 94 | 95 | 32 | 29 | 12 | 5.15E-07 | >1.00E-04 | >1.00E-04 |

TABLE II-continued

Colchicine in the NCI Anti-Cancer Screen

| Prostate Cancer | | | | | | | | |
|---|---|---|---|---|---|---|---|---|
| PC-3 | 71 | 16 | 5 | 8 | 6 | 2.38E-08 | >1.00E-04 | >1.00E-04 |
| DU-145 | 96 | 64 | 63 | 49 | 19 | 8.37E-06 | >1.00E-04 | >1.00E-04 |
| Breast Cancer | | | | | | | | |
| MCF7 | 54 | 19 | 18 | 17 | 8 | 1.30E-08 | >1.00E-04 | >1.00E-04 |
| MDA-MB-231/ATCC | 65 | 57 | 60 | 48 | 23 | 7.13E-06 | >1.00E-04 | >1.00E-04 |
| MDA-MB-435 | 31 | −31 | −22 | −28 | −34 | <1.00E-08 | 3.15E-08 | >1.00E-04 |
| MDA-N | 38 | 26 | 25 | 27 | −9 | <1.00E-08 | 5.62E-05 | >1.00E-04 |
| BT-549 | 69 | 39 | 42 | 48 | −21 | 4.25E-08 | 5.02E-05 | >1.00E-04 |
| T-47D | 81 | 89 | 79 | 82 | 42 | 6.14E-05 | >1.00E-04 | >1.00E-04 |

TABLE III

7-Acetamido-Allocolchinone in the NCI Anti-Cancer Screen

| Panel/Cell Line | Time | | Log10 Concentration Mean Optical Densities | | | | |
|---|---|---|---|---|---|---|---|
| | Zero | Ctrl | −10.0 | −9.0 | −8.0 | −7.0 | −6.0 |
| Leukemia | | | | | | | |
| CCRF-CEM | 0.674 | 1.409 | 1.281 | 0.570 | 0.504 | 0.467 | 0.463 |
| HL-60 (TB) | 0.693 | 1.497 | 1.390 | 0.417 | 0.401 | 0.382 | 0.352 |
| K-562 | 0.324 | 1.190 | 1.074 | 0.324 | 0.325 | 0.329 | 0.308 |
| MOLT-4 | 0.331 | 1.575 | 1.939 | 1.170 | 0.811 | 0.784 | 0.747 |
| RPMI-8226 | 0.959 | 1.552 | 1.487 | 0.785 | 0.793 | 0.785 | 0.770 |
| SR | 0.579 | 0.987 | 0.694 | 0.354 | 0.328 | 0.324 | 0.307 |
| Non-Small Cell Lung Cancer | | | | | | | |
| A549/ATCC | 0.273 | 1.131 | 1.171 | 1.058 | 0.505 | 0.471 | 0.471 |
| EKVX | 0.418 | 0.995 | 1.010 | 0.572 | 0.524 | 0.505 | 0.532 |
| HOP-62 | 0.525 | 1.357 | 1.362 | 1.165 | 0.922 | 0.920 | 0.895 |
| HOP-92 | 0.707 | 0.993 | 0.976 | 0.817 | 0.537 | 0.777 | 0.740 |
| NCI-H226 | 0.553 | 1.012 | 1.026 | 0.771 | 0.522 | 0.451 | 0.403 |
| NCI-H23 | 0.358 | 0.952 | 0.959 | 0.505 | 0.482 | 0.521 | 0.566 |
| NCI-H322M | 0.405 | 0.595 | 0.918 | 0.482 | 0.542 | 0.494 | 0.532 |
| NCI-H460 | 0.236 | 1.943 | 1.999 | 1.661 | 0.590 | 0.502 | 0.427 |
| NCI-H522 | 0.713 | 1.502 | 1.470 | 0.685 | 0.718 | 0.694 | 0.731 |
| Colon Cancer | | | | | | | |
| COLO 205 | 0.256 | 1.234 | 1.252 | 0.773 | 0.266 | 0.195 | 0.092 |
| HCC-2998 | 0.678 | 1.392 | 1.555 | 1.465 | 1.372 | 0.559 | 0.650 |
| HCT-116 | 0.504 | 2.699 | 2.839 | 0.971 | 0.758 | 0.809 | 0.487 |
| HCT-15 | 0.506 | 1.913 | 1.817 | 1.488 | 0.944 | 0.817 | 0.794 |
| HT29 | 0.137 | 0.555 | 0.594 | 0.093 | 0.099 | 0.077 | 0.094 |
| KM12 | 0.384 | 1.622 | 1.252 | 0.685 | 0.571 | 0.467 | 0.470 |
| SW-620 | 0.190 | 1.096 | 1.010 | 0.390 | 0.396 | 0.409 | 0.395 |
| CNS Cancer | | | | | | | |
| SF-268 | 0.521 | 1.391 | 1.321 | 0.368 | 0.321 | 0.327 | 0.836 |
| SF-295 | 0.350 | 0.959 | 0.983 | 0.445 | 0.385 | 0.415 | 0.405 |
| SF-539 | 0.491 | 1.706 | 1.711 | 0.717 | 0.509 | 0.504 | 0.563 |
| SNB-19 | 0.463 | 1.464 | 1.433 | 1.093 | 0.727 | 0.741 | 0.726 |
| SNB-75 | 0.458 | 0.324 | 0.799 | 0.320 | 0.604 | 0.623 | 0.642 |
| U251 | 0.222 | 1.050 | 1.016 | 0.409 | 0.395 | 0.399 | 0.363 |
| Melanoma | | | | | | | |
| LOX IMVI | 0.067 | 0.530 | 0.467 | 0.261 | 0.137 | 0.157 | 0.139 |
| MALME-3M | 0.459 | 0.806 | 0.775 | 0.644 | 0.538 | 0.536 | 0.637 |
| M14 | 0.100 | 0.790 | 0.720 | 0.242 | 0.270 | 0.237 | 0.333 |
| SK-MEL-2 | 0.572 | 1.211 | 1.160 | 0.342 | 0.333 | 0.324 | 0.763 |
| SK-MEL-28 | 0.537 | 1.325 | 1.242 | 0.348 | 0.945 | 0.959 | 1.955 |
| SK-MEL-5 | 0.241 | 1.167 | 0.915 | 0.520 | 0.401 | 0.277 | 0.302 |
| UACC-157 | 0.643 | 1.396 | 1.303 | 1.166 | 1.203 | 1.135 | 1.210 |
| UACC-62 | 0.515 | 1.545 | 1.439 | 0.592 | 0.351 | 0.883 | 0.904 |
| Ovarian Cancer | | | | | | | |
| IGR-OV1 | 0.362 | 1.174 | 1.251 | 0.766 | 0.557 | 0.517 | 0.451 |
| OVCAR-3 | 0.352 | 0.934 | 0.914 | 0.315 | 0.354 | 0.384 | 0.395 |
| OVCAR-4 | 0.597 | 1.384 | 1.322 | 1.085 | 1.048 | 1.036 | 1.003 |

TABLE III-continued

7-Acetamido-Allocolchinone in the NCI Anti-Cancer Screen

| | | | | | | | |
|---|---|---|---|---|---|---|---|
| OVCAR-5 | 0.330 | 0.925 | 0.944 | 0.573 | 0.565 | 0.557 | 0.574 |
| OVCAR-6 | 0.204 | 0.737 | 0.716 | 0.340 | 0.240 | 0.255 | 0.252 |
| SK-OV-3 | 0.633 | 1.321 | 1.309 | 0.936 | 0.715 | 0.765 | 0.732 |
| Renal Cancer | | | | | | | |
| 786-0 | 0.254 | 1.153 | 1.122 | 0.808 | 0.543 | 0.591 | 0.611 |
| A498 | 0.950 | 1.159 | 1.111 | 1.101 | 1.039 | 0.866 | 0.855 |
| ACHN | 0.393 | 1.446 | 1.487 | 1.138 | 1.039 | 0.885 | 0.889 |
| RXF-393 | 0.577 | 1.393 | 1.398 | 0.918 | 0.861 | 1.049 | 1.074 |
| SN12C | 0.357 | 1.195 | 1.194 | 0.516 | 0.537 | 0.616 | 0.616 |
| TK-10 | 0.433 | 0.376 | 0.357 | 0.721 | 0.720 | 0.723 | 0.746 |
| UTO-31 | 0.491 | 1.242 | 1.233 | 1.167 | 0.876 | 0.883 | 0.810 |
| Prostate Cancer | | | | | | | |
| PC-3 | 0.480 | 1.480 | 1.455 | 0.814 | 0.755 | 0.730 | 0.696 |
| DU-145 | 0.495 | 1.641 | 1.567 | 1.128 | 0.599 | 0.472 | 0.432 |
| Breast Cancer | | | | | | | |
| MCF7 | 0.183 | 0.619 | 0.595 | 0.243 | 0.229 | 0.216 | 0.232 |
| MCF7/ADR-RES | 0.521 | 1.491 | 1.405 | 1.232 | 1.064 | 0.386 | 0.885 |
| MDA-MB-231/ATCC | 0.358 | 0.737 | 0.592 | 0.397 | 0.348 | 0.374 | 0.329 |
| HS 575T | 0.519 | 0.910 | 0.919 | 0.624 | 0.671 | 0.666 | 0.529 |
| MDA-MB-135 | 0.308 | 0.957 | 0.733 | 0.167 | 0.226 | 0.223 | 0.200 |
| MDA-N | 0.232 | 1.125 | 0.905 | 0.106 | 0.145 | 0.138 | 0.155 |
| BT-549 | 0.545 | 1.072 | 1.037 | 0.574 | 0.531 | 0.789 | 0.786 |
| T-47D | 0.584 | 1.896 | 1.539 | 1.259 | 1.376 | 1.441 | 1.393 |

| | Log10 Concentration Percent Growth | | | | | | | |
|---|---|---|---|---|---|---|---|---|
| Panel/Cell Line | −10.0 | −9.0 | −8.0 | −7.0 | −6.0 | GI50 | TGI | LC50 |
| Leukemia | | | | | | | | |
| CCRF-CEM | 63 | −15 | −25 | −31 | −31 | 2.15E-10 | 6.96E-10 | >1.00E-06 |
| HL-60 (TB) | 87 | −40 | −42 | −45 | −49 | 1.95E-10 | 4.54E-10 | >1.00E-06 |
| K-562 | 87 | 0 | 0 | 1 | −5 | 2.65E-10 | 1.26E-07 | >1.00E-06 |
| MOLT-4 | 106 | 32 | −1 | −6 | −10 | 5.76E-10 | 9.17E-09 | >1.00E-06 |
| RPMI-8226 | 89 | −18 | −17 | −18 | −20 | 2.31E-10 | 6.76E-10 | >1.00E-06 |
| SR | 28 | −39 | −43 | −44 | −47 | <1.00E-10 | 3.63E-10 | >1.00E-06 |
| Non-Small Cell Lung Cancer | | | | | | | | |
| A549/ATCC | 105 | 91 | 27 | 23 | 23 | 4.39E-09 | >1.00E-06 | >1.00E-06 |
| EKVX | 103 | 44 | 36 | 32 | 37 | 7.90E-10 | >1.00E-06 | >1.00E-06 |
| HOP-52 | 101 | 77 | 47 | 46 | 44 | 7.68E-09 | >1.00E-06 | >1.00E-06 |
| HOP-92 | 94 | 36 | 45 | 24 | 11 | 6.18E-10 | >1.00E-06 | >1.00E-06 |
| NCI-H226 | 103 | 47 | −6 | −19 | −27 | 9.00E-10 | 7.57E-09 | >1.00E-06 |
| NCI-H23 | 101 | 23 | 20 | 26 | 34 | 4.56E-10 | >1.00E-06 | >1.00E-06 |
| NCI-H322M | 104 | 15 | 25 | 18 | 26 | 4.09E-10 | >1.00E-06 | >1.00E-06 |
| NCI-H460 | 103 | 83 | 21 | 16 | 11 | 3.42E-09 | >1.00E-06 | >1.00E-06 |
| NCI-H522 | 96 | 22 | 1 | −3 | 2 | 4.16E-10 | | >1.00E-06 |
| Colon Cancer | | | | | | | | |
| COLO 205 | 97 | 50 | 1 | −25 | −64 | 1.01E-09 | 1.05E-06 | 4.36E-07 |
| HCC-2998 | 123 | 110 | 97 | 25 | −4 | 4.53E-08 | 7.24E-07 | >1.00E-06 |
| HCT-116 | 106 | 21 | 12 | 14 | −3 | 4.60E-10 | 6.31E-07 | >1.00E-06 |
| HCT-15 | 93 | 70 | 31 | 22 | 20 | 3.25E-09 | >1.00E-06 | >1.00E-06 |
| HT29 | 109 | −32 | −35 | −44 | −31 | 2.63E-10 | 5.93E-10 | >1.00E-06 |
| KM12 | 70 | 24 | 15 | 7 | 7 | 2.75E-10 | >1.00E-06 | >1.00E-06 |
| SW-620 | 90 | 22 | 23 | 24 | 23 | 3.90E-10 | >1.00E-06 | >1.00E-06 |
| CNS Cancer | | | | | | | | |
| SF-268 | 92 | 40 | 34 | 35 | 36 | 6.39E-10 | >1.00E-06 | >1.00E-06 |
| SF-295 | 104 | 16 | 6 | 11 | 9 | 4.09E-10 | >1.00E-06 | >1.00E-06 |
| SF-539 | 100 | 19 | 10 | 1 | 6 | 4.13E-10 | >1.00E-06 | >1.00E-06 |
| SNB-19 | 99 | 63 | 25 | 25 | 36 | 2.26E-09 | >1.00E-06 | >1.00E-06 |
| SNB-75 | 96 | 17 | 41 | 46 | 52 | | >1.00E-06 | >1.00E-06 |
| U251 | 96 | 23 | 22 | 22 | 18 | 4.30E-10 | >1.00E-06 | >1.00E-06 |
| Melanoma | | | | | | | | |
| LOX IMVI | 86 | 39 | 22 | 16 | 12 | 5.90E-10 | >1.00E-06 | >1.00E-06 |
| MALME-3M | 91 | 53 | 52 | 51 | 57 | >1.00E-06 | >1.00E-06 | >1.00E-06 |
| M14 | 55 | 7 | 12 | 6 | 6 | 2.96E-10 | >1.00E-06 | >1.00E-06 |
| SK-MEL-2 | 92 | 42 | 49 | 39 | 33 | 7.02E-10 | >1.00E-06 | 1.00E-06 |
| SK-MEL-28 | 39 | 39 | 52 | 53 | 57 | | >1.00E-06 | >1.00E-06 |

TABLE III-continued

7-Acetamido-Allocolchinone in the NCI Anti-Cancer Screen

| | | | | | | | | |
|---|---|---|---|---|---|---|---|---|
| SK-MEL-5 | 82 | 34 | 19 | 4 | | 4.57E-10 | >1.00E-06 | >1.00E-06 |
| UACC-157 | 88 | 69 | 74 | 65 | 75 | >1.00E-06 | >1.00E-06 | >1.00E-06 |
| UACC-62 | 95 | 37 | 33 | 36 | 38 | 5.88E-10 | >1.00E-06 | >1.00E-06 |
| Ovarian Cancer | | | | | | | | |
| IGR-OV1 | 110 | 50 | 24 | 19 | 11 | 9.93E-10 | >1.00E-06 | >1.00E-06 |
| OVCAR-3 | 97 | -11 | 2 | 5 | 7 | 3.72E-10 | | >1.00E-06 |
| OVCAR-4 | 92 | 62 | 57 | 56 | 32 | >1.00E-06 | >1.00E-06 | >1.00E-06 |
| OVCAR-5 | 103 | 41 | 39 | 43 | 41 | 7.13E-10 | >1.00E-06 | >1.00E-06 |
| OVCAR-6 | 96 | 25 | 7 | 9 | 9 | 4.49E-10 | >1.00E-06 | >1.00E-06 |
| SK-OV-3 | 95 | 44 | 12 | 19 | I?? | ??E-10 | >1.0)E-06 | >1.00E-06 |
| Renal Cancer | | | | | | | | |
| 786-0 | 96 | 51 | 32 | 36 | 39 | 2.41E-19 | >1.00E-06 | >1.00E-06 |
| A498 | 77 | 72 | 43 | -9 | -10 | 5.73E-19 | 6.74E-08 | >1.00E-06 |
| ACHN | 104 | 71 | 61 | 47 | 47 | 5.99E-08 | >1.00E-06 | >1.00E-06 |
| RXF-393 | 101 | 42 | 35 | 55 | 61 | >1;00E-06 | | >1.00E-06 |
| SN12C | 100 | 55 | 33 | 31 | 31 | 1.66E-09 | >1.00E-06 | >1.00E-06 |
| TK-10 | 98 | 65 | 65 | 65 | 71 | >1.00E-06 | >1.00E-06 | >1.00E-06 |
| UO-31 | 99 | 90 | 51 | 52 | 42 | 1.68E-07 | >1.00E-06 | >1.00E-06 |
| Prostate Cancer | | | | | | | | |
| PC-3 | 97 | 33 | 27 | 25 | 22 | 5.51E-10 | >1.00E-06 | >1.00E-06 |
| DU-145 | 94 | 55 | 9 | -5 | -13 | 1.30E-09 | 4.57E-08 | >1.00E-06 |
| Breast Cancer | | | | | | | | |
| MCF7 | 95 | 14 | 11 | 8 | 11 | 3.56E-10 | >1.00E-06 | >1.00E-06 |
| MCF7-ADR-RES | 91 | 73 | 56 | 38 | 37 | 2.11E-08 | >1.00E-06 | >1.00E-06 |
| MDA-MB-231/ATCC | 62 | 10 | -3 | 4 | -6 | 1.69E-10 | | >1.00E-06 |
| HS 575T | 103 | 27 | 39 | 38 | 3 | 4.94E-10 | >1.00E-06 | >1.00E-06 |
| MDA-MB-436 | 66 | -46 | -27 | -28 | -35 | 1.38E-10 | 3.88E-10 | >1.00E-06 |
| MDA-N | 75 | -54 | -33 | -41 | -33 | 1.57E-10 | 3.81E-10 | |
| BT-549 | 93 | 62 | 54 | 46 | 46 | 3.48E-06 | >1.00E-06 | >1.00E-06 |
| T-47D | 96 | 54 | 60 | 65 | 62 | >1.00E-06 | >1.00E-06 | >1.00E-06 |

TABLE IV

| | Time | | Log10 Concentration Mean Optical Densities | | | | |
|---|---|---|---|---|---|---|---|
| Panel/Cell Line | Zero | Ctrl | -8.0 | -7.0 | -6.0 | -5.0 | -4.0 |
| Leukemia | | | | | | | |
| CCRF-CEM | 0.307 | 1.262 | 0.310 | 0.297 | 0.299 | 0.315 | 0.316 |
| HL-60 (TB) | 0.530 | 2.120 | 0.438 | 0.405 | 0.407 | 0.411 | 0.412 |
| K-562 | 0.183 | 1.214 | 0.241 | 0.220 | 0.240 | 0.256 | 0.228 |
| MOLT-4 | 0.399 | 1.390 | 0.562 | 0.517 | 0.523 | 0.491 | 0.421 |
| RPMI-8226 | 0.615 | 1.828 | 0.790 | 0.752 | 0.717 | 0.695 | 0.560 |
| SR | 0.280 | 0.920 | 0.278 | 0.258 | 0.251 | 0.255 | 0.260 |
| Non-Small Cell Lung Cancer | | | | | | | |
| A549/ATCC | 0.353 | 1.621 | 1.062 | 0.526 | 0.502 | 0.500 | 0.519 |
| EKVX | 0.410 | 1.110 | 0.574 | 0.555 | 0.631 | 0.606 | 0.596 |
| HOP-62 | 0.441 | 1.084 | 0.582 | 0.604 | 0.673 | 0.706 | 0.720 |
| HOP-92 | 0.749 | 1.186 | 1.015 | 0.825 | 0.822 | 0.845 | 0.950 |
| NCI-H226 | 0.595 | 1.103 | 0.629 | 0.489 | 0.490 | 0.465 | 0.507 |
| NCI-H23 | 0.212 | 1.927 | 0.267 | 0.215 | 0.270 | 0.251 | 0.207 |
| NCI-H322M | 0.458 | 0.177 | 0.725 | 0.725 | 0.814 | 0.763 | 0.670 |
| NCI-H460 | 0.209 | 1.360 | 0.289 | 0.203 | 0.225 | 0.229 | 0.214 |
| NCI-H522 | 0.399 | 1.022 | 0.220 | 0.194 | 0.394 | 0.213 | 0.227 |
| Colon Cancer | | | | | | | |
| COLO 205 | 0.276 | 1.133 | 0.355 | 0.171 | 0.032 | 0.026 | 0.006 |
| HCC-2998 | 0.655 | 1.297 | 0.888 | 0.522 | 0.484 | 0.510 | 0.300 |
| HCT-116 | 0.171 | 1.652 | 0.352 | 0.270 | 0.264 | 0.253 | 0.191 |
| HCT-15 | 0.382 | 1.944 | 0.468 | 0.318 | 0.338 | 0.325 | 0.510 |
| HT29 | 0.276 | 1.519 | 0.242 | 0.214 | 0.300 | 0.267 | 0.278 |
| KM12 | 0.205 | 1.276 | 0.340 | 0.175 | 0.139 | 0.150 | 0.132 |
| SW-620 | 0.172 | 1.109 | 0.370 | 0.394 | 0.391 | 0.433 | 0.414 |

TABLE IV-continued

| | | | | | | | |
|---|---|---|---|---|---|---|---|
| CNS Cancer | | | | | | | |
| SF-268 | 0.499 | 1.281 | 0.837 | 0.725 | 0.641 | 0.607 | 0.446 |
| SF-295 | 0.337 | 1.325 | 0.377 | 0.368 | 0.404 | 0.436 | 0.545 |
| SF-539 | 0.574 | 1.915 | 0.596 | 0.498 | 0.530 | 0.502 | 0.528 |
| SNB-19 | 0.616 | 1.699 | 0.813 | 0.742 | 0.760 | 0.691 | 0.582 |
| SNB-75 | 0.603 | 0.856 | 0.434 | 0.380 | 0.216 | 0.325 | 0.206 |
| U251 | 0.216 | 0.904 | 0.222 | 0.181 | 0.183 | 0.152 | 0.150 |
| Melanoma | | | | | | | |
| LOX IMVI | 0.074 | 0.544 | 0.222 | 0.098 | 0.096 | 0.079 | 0.092 |
| MALME-3M | 0.610 | 1.342 | 0.869 | 0.722 | 0.725 | 0.785 | 0.554 |
| M14 | 0.249 | 0.947 | 0.220 | 0.194 | 0.202 | 0.184 | 0.177 |
| SK-MEL-2 | 0.431 | 0.924 | 0.559 | 0.392 | 0.453 | 0.357 | 0.406 |
| SK-MEL-28 | 0.741 | 1.207 | 0.721 | 0.759 | 0.868 | 0.867 | 0.874 |
| SK-MEL-5 | 0.228 | 1.117 | 0.348 | 0.216 | 0.259 | 0.237 | 0.214 |
| UACC-257 | 0.549 | 1.354 | 0.946 | 0.837 | 0.878 | 0.826 | 0.874 |
| UACC-62 | 0.508 | 1.831 | 0.757 | 0.919 | 0.999 | 0.980 | 0.856 |
| Ovarian Cancer | | | | | | | |
| IGR-OVI | 0.392 | 1.334 | 0.660 | 0.525 | 0.544 | 0.594 | 0.544 |
| OVCAR-3 | 0.240 | 0.638 | 0.201 | 0.168 | 0.178 | 0.161 | 0.139 |
| OVCAR-4 | 0.487 | 1.015 | 0.824 | 0.808 | 0.745 | 0.741 | 0.585 |
| OVCAR-5 | 0.365 | 0.908 | 0.456 | 0.494 | 0.498 | 0.473 | 0.431 |
| OVCAR-8 | 0.286 | 1.215 | 0.412 | 0.277 | 0.291 | 0.286 | 0.291 |
| SK-OV-3 | 0.669 | 1.223 | 0.780 | 0.603 | 0.508 | 0.540 | 0.426 |
| Renal Cancer | | | | | | | |
| 786-0 | 0.186 | 0.881 | 0.339 | 0.332 | 0.289 | 0.281 | 0.213 |
| A498 | 1.084 | 1.336 | 1.214 | 0.676 | 0.648 | 0.711 | 0.470 |
| ACHN | 0.532 | 1.226 | 0.785 | 0.554 | 0.502 | 0.475 | 0.420 |
| CAKI-1 | 0.318 | 1.193 | 0.665 | 0.589 | 0.574 | 0.553 | 0.461 |
| RXF-393 | 0.411 | 0.868 | 0.492 | 0.578 | 0.590 | 0.549 | 0.415 |
| SN12C | 0.614 | 1.617 | 0.843 | 0.683 | 0.674 | 0.748 | 0.738 |
| TK-10 | 1.061 | 1.707 | 1.406 | 1.503 | 1.595 | 1.503 | 1.222 |
| UO-31 | 0.698 | 1.628 | 1.188 | 1.050 | 0.924 | 0.907 | 0.668 |
| Prostate Cancer | | | | | | | |
| PC-3 | 0.378 | 1.136 | 0.505 | 0.442 | 0.304 | 0.300 | 0.313 |
| DU-145 | 0.344 | 1.213 | 0.387 | 0.231 | 0.319 | 0.201 | 0.194 |
| Breast Cancer | | | | | | | |
| MCF7 | 0.197 | 0.477 | 0.173 | 0.156 | 0.164 | 0.165 | 0.154 |
| MCF7/ADR-RES | 0.551 | 1.257 | 0.875 | 0.170 | 0.227 | 0.249 | 0.431 |
| MDA-MB-231/ATCC | 0.276 | 0.685 | 0.339 | 0.275 | 0.275 | 0.288 | 0.335 |
| HS-578T | 0.511 | 1.079 | 0.571 | 0.638 | 0.656 | 0.661 | 0.546 |
| MDA-MB-435 | 0.238 | 1.143 | 0.109 | 0.130 | 0.137 | 0.134 | 0.158 |
| MDA-N | 0.309 | 1.429 | 0.147 | 0.154 | 0.162 | 0.155 | 0.166 |
| BT-549 | 0.389 | 0.891 | 0.560 | 0.473 | 0.491 | 0.456 | 0.393 |
| T-47D | 0.700 | 1.720 | 1.066 | 1.445 | 1.513 | 1.359 | 1.408 |

| | Log10 Concentration Percent Growth | | | | | | | |
|---|---|---|---|---|---|---|---|---|
| Panel/Cell Line | −8.0 | −7.0 | −6.0 | −5.0 | −4.0 | GI50 | TGI | LC50 |
| Leukemia | | | | | | | | |
| CCRF-CEM | 0 | −3 | −2 | 1 | 1 | <1.00E-08 | | >1.00E-04 |
| HL-60 (TB) | −17 | −24 | −23 | −22 | −22 | <1.00E-08 | <1.00E-08 | >1.00E-04 |
| K-562 | 6 | 4 | 6 | 7 | 4 | <1.00E-08 | >1.00E-04 | >1.00E-04 |
| MOLT-4 | 16 | 12 | 12 | 9 | 2 | <1.00E-08 | >1.00E-04 | >1.00E-04 |
| RPMI-8226 | 14 | 11 | 8 | 7 | −9 | <1.00E-08 | 2.66E-05 | >1.00E-04 |
| SR | −1 | −8 | −11 | −9 | −7 | <1.00E-08 | <1.00E-08 | >1.00E-04 |
| Non-Small Cell Lung Cancer | | | | | | | | |
| A549/ATCC | 56 | 14 | 12 | 12 | 13 | 1.38E-08 | >1.00E-04 | >1.00E-04 |
| EKVX | 23 | 21 | 32 | 28 | 27 | <1.00E-08 | >1.00E-04 | >1.00E-04 |
| HOP-62 | 22 | 25 | 36 | 41 | 43 | <1.00E-08 | >1.00E-04 | >1.00E-04 |
| HOP-92 | 61 | 17 | 17 | 22 | 46 | 1.76E-08 | >1.00E-04 | >1.00E-04 |
| NCI-H226 | 7 | −18 | −18 | −22 | −15 | <1.00E-08 | 1.89E-08 | >1.00E-04 |
| NCI-H23 | 8 | 0 | 8 | 5 | −3 | <1.00E-08 | 4.73E-05 | >1.00E-04 |
| NCI-H322M | 37 | 37 | 50 | 43 | 30 | <1.00E-08 | >1.00E-04 | >1.00E-04 |
| NCI-H46G | 7 | −3 | 1 | 2 | 0 | <1.00E-08 | | >1.00E-04 |
| NCI-H522 | −45 | −51 | −1 | −47 | −43 | <1.00E-08 | <1.00E-08 | |
| Colon Cancer | | | | | | | | |
| COLO 205 | 9 | −38 | −88 | −91 | −98 | <1.00E-08 | 1.56E-08 | 1.72E-07 |

TABLE IV-continued

| | | | | | | | | |
|---|---|---|---|---|---|---|---|---|
| HCC-2998 | 36 | −20 | −26 | −22 | −54 | <1.00E-08 | 4.39E-08 | 7.40E-05 |
| HCT-116 | 12 | 7 | 6 | 6 | 1 | <1.00E-08 | >1.00E-04 | >1.00E-04 |
| HCT-15 | 6 | −17 | −12 | −15 | 8 | <1.00E-08 | >1.00E-04 | |
| HT29 | −12 | −22 | 2 | −3 | 0 | <1.00E-08 | >1.00E-04 | |
| KM12 | 13 | −15 | −32 | −27 | −36 | <1.00E-08 | 2.91E-08 | >1.00E-04 |
| SW-620 | 21 | 24 | 23 | 28 | −26 | <1.00E-08 | >1.00E-04 | >1.00E-04 |
| CNS Cancer | | | | | | | | |
| SF-268 | 43 | 29 | 18 | 14 | −11 | <1.00E-08 | 3.67E-05 | >1.00E-04 |
| SF-295 | 4 | 3 | −7 | 10 | 21 | <1.00E-08 | >1.00E-04 | >1.00E-04 |
| SF-539 | 2 | −13 | −8 | −13 | −8 | <1.00E-08 | 1.29E-08 | >1.00E-04 |
| SNB-19 | 18 | 12 | 13 | 7 | −6 | <1.00E-08 | 3.56E-05 | >1.00E-04 |
| SNB-75 | −28 | −37 | −64 | −46 | −66 | <1.00E-08 | <1.00E-08 | |
| U251 | 1 | −16 | 16 | −30 | −31 | <1.00E-08 | 1.11E-08 | >1.00E-04 |
| Melanoma | | | | | | | | |
| LOX IMVI | 31 | 5 | 5 | 1 | 4 | <1.00E-08 | >1.00E-04 | >1.00E-04 |
| MALME-3M | 35 | 15 | 16 | 24 | −9 | <1.00E-08 | 5.25E-05 | >1.00E-04 |
| M14 | −12 | −22 | −19 | −26 | −29 | <1.00E-08 | <1.00E-08 | >1.00E-04 |
| SK-MEL-2 | 26 | −9 | 4 | −17 | −6 | <1.00E-08 | | >1.00E-04 |
| SK-MEL-28 | −3 | 4 | 27 | 27 | 29 | <1.00E-08 | | >1.00E-04 |
| SK-MEL-5 | 14 | −5 | 4 | 1 | −6 | <1.00E-08 | | >1.00E-04 |
| UACC-257 | 49 | 36 | 41 | 34 | 40 | <1.00E-08 | >1.00E-04 | >1.00E-04 |
| UACC-62 | 19 | 31 | 37 | 36 | 26 | <1.00E-08 | >1.00E-04 | >1.00E-04 |
| Ovarian Cancer | | | | | | | | |
| IGR-OV1 | 28 | 14 | 16 | 21 | 16 | <1.00E-08 | >1.00E-04 | >1.00E-04 |
| OVCAR-3 | −16 | −30 | −26 | −33 | −42 | <1.00E-08 | <1.00E-08 | >1.00E-04 |
| OVCAR-4 | 64 | 61 | 49 | 48 | 19 | 7.97E-07 | >1.00E-04 | >1.00E-04 |
| OVCAR-5 | 17 | 24 | 24 | 20 | 12 | <1.00E-08 | >1.00E-04 | >1.00E-04 |
| OVCAR-6 | 14 | −3 | 1 | 0 | 1 | <1.00E-08 | | >1.00E-04 |
| SK-OV-3 | 20 | −10 | −24 | −19 | −36 | <1.00E-8 | 4.68E-08 | >1.00E-04 |
| Renal Cancer | | | | | | | | |
| 786-0 | 22 | 21 | 15 | 14 | 4 | <1.00E-08 | >1.00E-04 | >1.00E-04 |
| A498 | 51 | −38 | −40 | −34 | −57 | 1.04E-08 | 3.78E-08 | 5.00E-05 |
| ACHN | 36 | 3 | −6 | −11 | −21 | <1.00E-08 | 2.30E-07 | >1.00E-04 |
| CAKI-1 | 40 | 31 | 29 | 27 | 16 | <1.00E-08 | >1.00E-04 | >1.00E-04 |
| RXF-393 | 18 | 36 | 39 | 30 | 1 | <1.00E-08 | >1.00E-04 | >1.00E-04 |
| SN12C | 23 | 7 | 6 | 13 | 12 | <1.00E-08 | >1.00E-04 | >1.00E-04 |
| TK-10 | 53 | 68 | 83 | 69 | 25 | 2.66E-05 | >1.00E-04 | >1.00E-04 |
| UO-31 | 53 | 38 | 24 | 22 | −4 | 1.52E-08 | 6.91E-05 | >1.00E-04 |
| Prostate Cancer | | | | | | | | |
| PC-3 | 17 | 8 | −20 | −21 | −17 | <1.00E-08 | 2.00E-07 | >1.00E-04 |
| DU-145 | 5 | −33 | −7 | −42 | −44 | <1.00E-08 | 1.35E-08 | >1.00E-04 |
| Breast Cancer | | | | | | | | |
| MCF7 | −12 | −21 | −17 | −16 | −22 | <1.00E-08 | <1.00E-08 | >1.00E-04 |
| MF7/ADR-RES | 46 | −69 | −59 | −55 | −22 | <1.00E-08 | 2.51E-08 | |
| MDA-MB-231/ATCC | 15 | 0 | 0 | 3 | 14 | <1.00E-08 | | >1.00E-04 |
| HS 578T | 11 | 22 | 26 | 26 | 6 | <1.00E-08 | >1.00E-04 | >1.00E-04 |
| MDA-MB-435 | −54 | −45 | −42 | −44 | −34 | <1.00E-08 | <1.00E-08 | |
| MDA-N | −53 | −50 | −48 | −50 | −46 | <1.00E-08 | <1.00E-08 | |
| BT-549 | 34 | 17 | 20 | 13 | 1 | <1.00E-08 | >1.00E-04 | >1.00E-04 |
| T-47D | 36 | 73 | 80 | 65 | 69 | | >1.00E-04 | >1.00E-04 |

TABLE V

| | Time | | Log10 Concentration Mean Optical Densities | | | | |
|---|---|---|---|---|---|---|---|
| Panel/Cell Line | Zero | Ctrl | −8.0 | −7.0 | −6.0 | −5.0 | −4.0 |
| Leukemia | | | | | | | |
| CCRF-CEM | 0.206 | 0.845 | 0.301 | 0.321 | 0.335 | 0.346 | 0.470 |
| HL-60 (TB) | 0.433 | 1.509 | 0.303 | 0.279 | 0.304 | 0.329 | 0.373 |
| MOLT-4 | 0.343 | 1.285 | 0.429 | 0.415 | 0.415 | 0.430 | 0.398 |
| RPMI-8226 | 0.786 | 1.734 | 0.927 | 0.903 | 0.887 | 0.868 | 0.899 |
| SR | 0.331 | 1.087 | 0.330 | 0.355 | 0.351 | 0.332 | 0.426 |
| Non-Small Cell Lung Cancer | | | | | | | |
| A549/ATCC | 0.343 | 1.796 | 0.599 | 0.596 | 0.539 | 0.606 | 0.510 |

TABLE V-continued

| | | | | | | | |
|---|---|---|---|---|---|---|---|
| EKVX | 0.398 | 1.050 | 0.596 | 0.591 | 0.620 | 0.659 | 0.502 |
| HOP-62 | 0.611 | 1.635 | 1.104 | 1.082 | 0.962 | 1.057 | 0.961 |
| HOP-92 | 0.747 | 1.115 | 0.748 | 0.723 | 0.756 | 0.736 | 0.780 |
| NCI-H226 | 0.543 | 1.162 | 0.455 | 0.429 | 0.416 | 0.437 | 0.505 |
| NCI-H23 | 0.389 | 1.538 | 0.319 | 0.419 | 0.438 | 0.319 | 0.264 |
| NCI-H322M | 0.592 | 1.602 | 0.939 | 0.946 | 0.952 | 0.915 | 0.783 |
| NCI-H460 | 0.159 | 1.495 | 0.175 | 0.192 | 0.163 | 0.159 | 0.171 |
| NCI-H522 | 0.462 | 1.132 | 0.248 | 0.245 | 0.255 | 0.190 | 0.126 |
| Colon Cancer | | | | | | | |
| COLO 205 | 0.222 | 1.140 | 0.173 | 0.074 | 0.038 | 0.034 | 0.004 |
| HCC-2998 | 0.372 | 1.484 | 0.623 | 0.617 | 0.605 | 0.600 | 0.183 |
| HCT-116 | 0.141 | 1.777 | 0.269 | 0.242 | 0.220 | 0.196 | 0.110 |
| HT29 | 0.090 | 0.766 | 0.063 | 0.082 | 0.078 | 0.087 | 0.048 |
| KM12 | 0.230 | 1.263 | 0.151 | 0.135 | 0.112 | 0.131 | 0.068 |
| SW-620 | 0.139 | 1.214 | 0.410 | 0.413 | 0.390 | 0.399 | 0.301 |
| CNS Cancer | | | | | | | |
| SF-268 | 0.436 | 1.393 | 0.742 | 0.737 | 0.722 | 0.680 | 0.444 |
| SF-295 | 0.362 | 1.981 | 0.580 | 0.535 | 0.527 | 0.557 | 0.665 |
| SF-539 | 0.597 | 1.820 | 0.549 | 0.531 | 0.504 | 0.528 | 0.615 |
| SNB-19 | 0.421 | 1.612 | 0.714 | 0.735 | 0.725 | 0.787 | 0.646 |
| SNB-75 | 0.557 | 0.966 | 0.588 | 0.641 | 0.653 | 0.565 | 0.632 |
| U251 | 0.195 | 1.149 | 0.232 | 0.267 | 0.262 | 0.244 | 0.247 |
| Melanoma | | | | | | | |
| LOX IMVI | 0.079 | 1.241 | 0.360 | 0.370 | 0.350 | 0.322 | 0.072 |
| MALME-3M | 0.333 | 1.091 | 0.464 | 0.492 | 0.465 | 0.525 | 0.452 |
| M14 | 0.255 | 1.163 | 0.293 | 0.264 | 0.270 | 0.294 | 0.375 |
| SK-MEL-2 | 0.492 | 1.222 | 0.377 | 0.472 | 0.475 | 0.570 | 0.617 |
| SK-MEL-28 | 0.514 | 1.599 | 1.034 | 1.061 | 1.098 | 1.082 | 1.140 |
| SK-MEL-5 | 0.086 | 1.113 | 0.110 | 0.120 | 0.100 | 0.108 | 0.046 |
| UACC-257 | 0.557 | 1.413 | 0.906 | 0.831 | 0.893 | 0.835 | 0.613 |
| UACC-62 | 0.390 | 1.485 | 0.694 | 0.715 | 0.719 | 0.728 | 0.613 |
| Ovarian Cancer | | | | | | | |
| IGR-OV1 | 0.373 | 1.184 | 0.547 | 0.535 | 0.521 | 0.536 | 0.363 |
| OVCAR-3 | 0.272 | 0.913 | 0.219 | 0.240 | 0.245 | 0.214 | 0.189 |
| OVCAR-4 | 0.414 | 0.864 | 0.677 | 0.641 | 0.629 | 0.601 | 0.472 |
| OVCAR-5 | 0.293 | 0.997 | 0.413 | 0.466 | 0.478 | 0.446 | 0.351 |
| OVCAR-8 | 0.231 | 1.071 | 0.162 | 0.168 | 0.184 | 0.185 | 0.174 |
| SK-OV-3 | 0.489 | 1.007 | 0.501 | 0.506 | 0.487 | 0.462 | 0.370 |
| Renal Cancer | | | | | | | |
| 786-0 | 0.171 | 0.676 | 0.348 | 0.328 | 0.298 | 0.290 | 0.232 |
| A498 | 0.775 | 1.446 | 0.865 | 0.811 | 0.794 | 0.837 | 0.582 |
| ACHN | 0.444 | 1.541 | 0.755 | 0.811 | 0.842 | 0.780 | 0.516 |
| CAKI-1 | 0.379 | 1.060 | 0.488 | 0.456 | 0.439 | 0.408 | 0.244 |
| RXF-393 | 0.462 | 1.088 | 0.642 | 0.690 | 0.711 | 0.623 | 0.524 |
| SN12C | 0.374 | 1.604 | 0.557 | 0.547 | 0.519 | 0.544 | 0.459 |
| TK-10 | 0.667 | 1.243 | 1.115 | 1.111 | 1.136 | 1.119 | 0.814 |
| UO-31 | 0.414 | 1.073 | 0.688 | 0.634 | 0.624 | 0.572 | 0.419 |
| Prostate Cancer | | | | | | | |
| PC-3 | 0.440 | 1.769 | 0.566 | 0.601 | 0.588 | 0.595 | 0.660 |
| DU-145 | 0.312 | 1.590 | 0.346 | 0.388 | 0.324 | 0.345 | 0.354 |
| Breast Cancer | | | | | | | |
| MCF7 | 0.186 | 0.584 | 0.212 | 0.169 | 0.235 | 0.201 | 0.178 |
| MCF7/ADR-RES | 0.455 | 1.361 | 0.227 | 0.266 | 0.284 | 0.266 | 0.352 |
| MDA-MB-231/ATCC | 0.265 | 0.655 | 0.250 | 0.239 | 0.264 | 0.273 | 0.333 |
| HS 578T | 0.636 | 1.146 | 0.857 | 0.792 | 0.854 | 0.845 | 0.666 |
| MDA-MB-435 | 0.165 | 1.074 | 0.093 | 0.094 | 0.089 | 0.090 | 0.141 |
| MDA-N | 0.229 | 1.481 | 0.155 | 0.140 | 0.147 | 0.165 | 0.257 |
| BT-549 | 0.462 | 1.080 | 0.623 | 0.686 | 0.647 | 0.605 | 0.410 |
| T-47D | 0.439 | 1.276 | 1.105 | 1.124 | 1.070 | 1.097 | 0.946 |

| | Log10 Concentration Percent Growth | | | | | | | |
|---|---|---|---|---|---|---|---|---|
| Panel/Cell Line | −8.0 | −7.0 | −6.0 | −5.0 | −4.0 | GI50 | TGI | LC50 |
| Leukemia | | | | | | | | |
| CCRF-CEM | 7 | 10 | 13 | 15 | 36 | <1.00E-08 | >1.00E-04 | >1.00E-04 |
| HL-60 (TB) | −30 | −36 | −30 | −24 | −14 | <1.00E-08 | <1.00E-08 | >1.00E-04 |
| MOLT-4 | 9 | 8 | 8 | 9 | 6 | <1.00E-08 | >1.00E-04 | >1.00E-04 |
| RPMI-8226 | 15 | 12 | 11 | 9 | 12 | <1.00E-08 | >1.00E-04 | >1.00E-04 |

TABLE V-continued

| | | | | | | | | |
|---|---|---|---|---|---|---|---|---|
| SR | 0 | 3 | 3 | 0 | 13 | <1.00E-08 | | >1.00E-04 |
| Non-Small Cell Lung Cancer | | | | | | | | |
| A549/ATCC | 18 | 17 | 14 | 18 | 11 | <1.00E-08 | >1.00E-04 | >1.00E-04 |
| EKVX | 30 | 30 | 34 | 40 | 16 | <1.00E-08 | >1.00E-04 | >1.00E-04 |
| HOP-62 | 48 | 46 | 34 | 44 | 34 | <1.00E-08 | >1.00E-04 | >1.00E-04 |
| HOP-92 | 0 | −3 | 2 | −1 | 9 | <1.00E-08 | | >1.00E-04 |
| NCI-H226 | −16 | −21 | −23 | −20 | −7 | <1.00E-08 | <1.00E-08 | >1.00E-04 |
| NCI-H23 | −18 | 3 | 4 | −18 | −32 | <1.00E-08 | | >1.00E-04 |
| NCI-H322M | 34 | 35 | 36 | 32 | 19 | <1.00E-08 | >1.00E-04 | >1.00E-04 |
| NCI-H460 | 1 | 2 | 0 | 0 | 1 | <1.00E-08 | >1.00E-04 | >1.00E-04 |
| NCI-H522 | −46 | −47 | −45 | −59 | −73 | <1.00E-08 | <1.00E-08 | 2.31E-06 |
| Colon Cancer | | | | | | | | |
| COLO 205 | −22 | −66 | −83 | −85 | −98 | <1.00E-08 | <1.00E-08 | 4.26E-08 |
| HCC-2998 | 23 | 22 | 21 | 21 | −51 | <1.00E-08 | 1.94E-05 | 9.70E-05 |
| HCT-116 | 8 | 6 | 5 | 3 | −22 | <1.00E-08 | 1.35E-05 | >1.00E-04 |
| HT29 | −31 | −9 | −14 | −4 | −46 | <1.00E-08 | <1.00E-08 | >1.00E-04 |
| KM12 | −34 | −41 | −51 | −43 | −70 | <1.00E-08 | <1.00E-08 | |
| SW-620 | 25 | 26 | 23 | 24 | 15 | <1.00E-08 | >1.00E-04 | >1.00E-04 |
| CNS Cancer | | | | | | | | |
| SF-268 | 32 | 31 | 30 | 25 | 1 | <1.00E-08 | >1.00E-04 | >1.00E-04 |
| SF-295 | 13 | 11 | 10 | 12 | 19 | <1.00E-08 | >1.00E-04 | >1.00E-04 |
| SF-539 | −8 | −11 | −16 | −12 | 1 | <1.00E-08 | | >1.00E-04 |
| SNB-19 | 25 | 26 | 26 | 31 | 19 | <1.00E-08 | >1.00E-04 | >1.00E-04 |
| SNB-75 | 8 | 21 | 23 | 2 | 18 | <1.00E-08 | >1.00E-04 | >1.00E-04 |
| U251 | 4 | 8 | 7 | 5 | 5 | <1.00E-08 | >1.00E-04 | >1.00E-04 |
| Melanoma | | | | | | | | |
| LOX IMVI | 24 | 25 | 23 | 21 | −9 | <1.00E-08 | 4.87E-05 | >1.00E-04 |
| MALME-3M | 17 | 21 | 17 | 25 | 16 | <1.00E-08 | >1.00E-04 | >1.00E-04 |
| M14 | 4 | 1 | 2 | 4 | 13 | <1.00E-08 | >1.00E-04 | >1.00E-04 |
| SK-MEL-2 | −23 | −4 | −3 | 11 | 17 | <1.00E-08 | | >1.00E-04 |
| SK-MEL-28 | 48 | 50 | 54 | 52 | 58 | | >1.00E-04 | >1.00E-04 |
| SK-MEL-5 | 2 | 3 | 1 | 2 | −47 | <1.00E-08 | 1.11E-05 | >1.00E-04 |
| UACC-257 | 41 | 32 | 39 | 32 | 7 | <1.00E-08 | >1.00E-04 | >1.00E-04 |
| UACC-62 | 28 | 30 | 30 | 31 | 20 | <1.00E-08 | >1.00E-04 | >1.00E-04 |
| Ovarian Cancer | | | | | | | | |
| IGR-OV1 | 21 | 20 | 18 | 20 | −3 | <1.00E-08 | 7.72E-05 | >1.00E-04 |
| OVCAR-3 | −19 | −12 | −10 | −21 | −30 | <1.00E-08 | <1.00E-08 | >1.00E-04 |
| OVCAR-4 | 58 | 51 | 48 | 42 | 13 | 1.65E-07 | >1.00E-04 | >1.00E-04 |
| OVCAR-5 | 17 | 25 | 26 | 22 | 8 | <1.00E-08 | >1.00E-04 | >1.00E-04 |
| OVCAR-8 | −30 | −27 | −21 | −20 | −25 | <1.00E-08 | >1.00E-08 | >1.00E-04 |
| SK-OV-3 | 2 | 3 | 0 | −6 | −24 | <1.00E-08 | 7.75E-07 | >1.00E-04 |
| Renal Cancer | | | | | | | | |
| 786-0 | 35 | 31 | 25 | 24 | 12 | <1.00E-08 | >1.00E-04 | >1.00E-04 |
| A498 | 13 | 5 | 3 | 9 | −25 | <1.00E-08 | 1.87E-05 | >1.00E-04 |
| ACHN | 28 | 33 | 36 | 31 | 7 | <1.00E-08 | >1.00E-04 | >1.00E-04 |
| CAKI-1 | 16 | 11 | 9 | 4 | −36 | <1.00E-08 | 1.27E-05 | >1.00E-04 |
| RXF-393 | 29 | 36 | 40 | 26 | 10 | <1.00E-08 | >1.00E-04 | >1.00E-04 |
| SN12C | 15 | 14 | 12 | 14 | 7 | <1.00E-08 | >1.00E-04 | >1.00E-04 |
| TK-10 | 78 | 77 | 81 | 79 | 26 | 3.45E-05 | >1.00E-04 | >1.00E-04 |
| UO-31 | 42 | 33 | 32 | 24 | 1 | <1.00E-08 | >1.00E-04 | >1.00E-04 |
| Prostate Cancer | | | | | | | | |
| PC-3 | 9 | 12 | 11 | 12 | 17 | <1.00E-08 | >1.00E-04 | >1.00E-04 |
| DU-145 | 3 | 6 | 1 | 3 | 3 | <1.00E-08 | >1.00E-04 | >1.00E-04 |
| Breast Cancer | | | | | | | | |
| MCF7 | 6 | −9 | 12 | 4 | −4 | <1.00E-08 | | >1.00E-04 |
| MF7/ADR-RES | −50 | −42 | −37 | −42 | −23 | <1.00E-08 | <1.00E-08 | |
| MDA-MB-231/ATCC | −6 | −10 | −1 | 2 | 18 | <1.00E-08 | | >1.00E-04 |
| HS 578T | 43 | 31 | 43 | 41 | 6 | <1.00E-08 | >1.00E-04 | >1.00E-04 |
| MDA-MB-435 | −44 | −43 | −46 | −45 | −15 | <1.00E-08 | <1.00E-08 | |
| MDA-N | −32 | −39 | −36 | −28 | 2 | <1.00E-08 | | >1.00E-04 |
| BT-549 | 26 | 36 | 30 | 23 | 11 | <1.00E-08 | 4.69E-05 | >1.00E-04 |
| T-47D | 80 | 82 | 75 | 79 | 61 | >1.00E-04 | >1.00E-04 | >1.00E-04 |

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. An inhibitor of microtubule assembly comprising an allocolchinone.

2. The inhibitor of claim 1 wherein the allocolchinone is represented by a structure selected from the group consisting of:

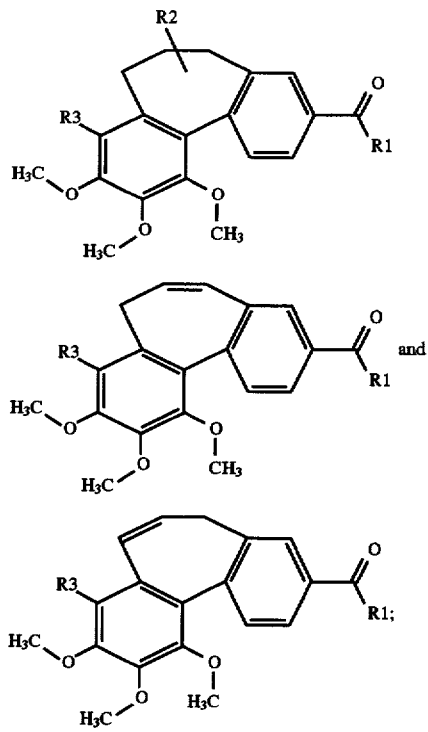

wherein:
R1 is selected from the group consisting of methyl, ethyl, fluorinated methyl and fluorinated ethyl;
R2 is selected from the group consisting of —H, =O, —NH$_2$, —NHR', hydroxy, —OR', —SH, —O—CO—R', —O—CO—R", —SR', —NH—CO—R', —NH—CO—R", —NH—CO—O—R', —NH—CHO, —NH—CHS, —NH—CO—CH$_2$OH, —NH—CS—R', and lower alkyl;
R3 is selected from the group consisting of —H, —OR', —CHCl$_2$, —CN, —NHCHO, —CH$_2$OH, lower alkyl, —NH—CO—R', —CH$_2$N(CH$_3$)$_2$, —COOR', and —O—CO—R'; and
R' is a lower alkyl group and R" is a substituted lower alkyl group.

3. The inhibitor of claim 2 wherein the allocolchinone is represented by the following structure:

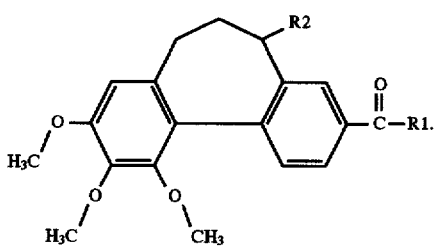

4. The inhibitor of claim 3 wherein R1 is methyl and R2 is —NH—CO—R'.

5. The inhibitor of claim 4 wherein R1 is methyl and R2 is —NH—CO—CH$_2$—CH$_2$—CH$_3$.

6. The inhibitor of claim 4 wherein R1 is methyl and R2 is —NH—CO—CH$_3$.

7. A method of inhibiting the assembly of tubulin into microtubules, comprising contacting tubulin with an inhibitory amount of an allocolchinone represented by a structure selected from the group consisting of:

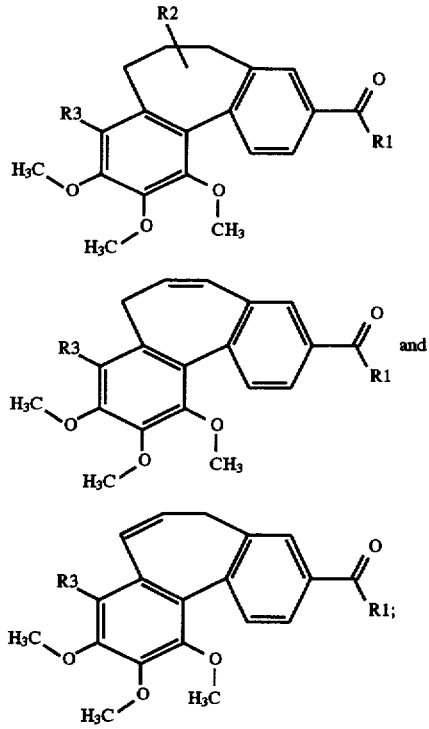

wherein:
R1 is selected from the group consisting of methyl, ethyl, fluorinated methyl and fluorinated ethyl; and
R2 is selected from the group consisting of —H, =O, —NH$_2$, —NHR', hydroxy, —OR', —SH, —O—CO—R', —O—CO—R", —SR', —NH—CO—R', —NH—CO—R", —NH—CO—O—R', —NH—CHO, —NH—CHS, —NH—CO—CH$_2$OH, —NH—CS—R', and lower alkyl;
R3 is selected from the group consisting of —H, —OR', —CHCl$_2$, —CN, —NHCHO, —CH$_2$OH, lower alkyl, —NH—CO—R', —CH$_2$N(CH$_3$)$_2$, —COOR', and —O—CO—R'; and
R' is a lower alkyl group and R" is a substituted lower alkyl group.

8. The method of claim 7 wherein the allocolchinone is represented by the following structure:

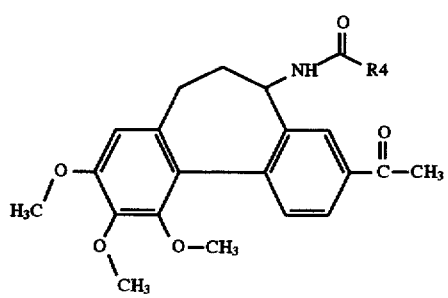

wherein R4 is methyl or propyl.

9. A method of treating cancer in an individual, comprising administering to the individual affected with cancer a composition comprising a therapeutically effective amount of an allocolchinone which inhibits microtubule assembly.

10. The method of claim 9 wherein the allocolchinone is represented by a structure selected from the group consisting of:

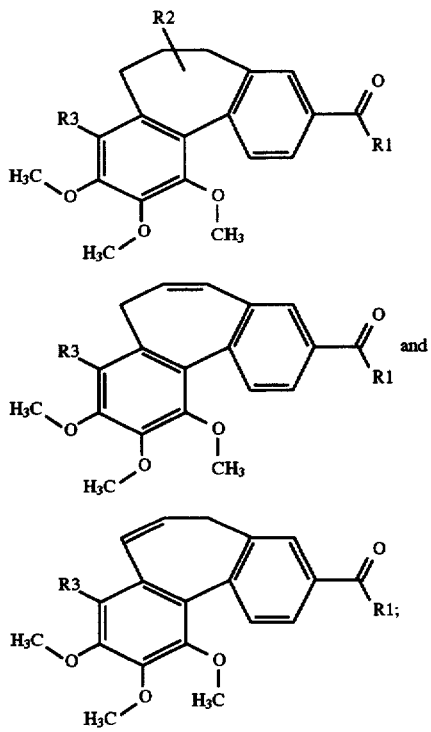

wherein:
R1 is selected from the group consisting of methyl, ethyl, fluorinated methyl and fluorinated ethyl;
R2 is selected from the group consisting of —H, =O, —NH₂, —NHR', hydroxy, —OR', —SH, —O—CO—R', —O—CO—R", —SR', —NH—CO—R', —NH—CO—R", —NH—CO—O—R', —NH—CHO, —NH—CHS, —NH—CO—CH₂OH, —NH—CS—R', and lower alkyl;
R3 is selected from the group consisting of —H, —OR', —CHCl₂, —CN, —NHCHO, —CH₂OH, lower alkyl, —NH—CO—R', —CH₂N(CH₃)₂, —COOR', and —O—CO—R'; and
R' is a lower alkyl group and R" is a substituted lower alkyl group.

11. The method of claim 10 wherein the allocolchinone is represented by the following structure:

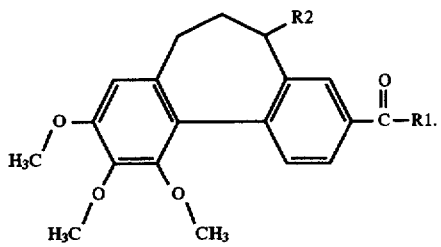

12. The method of claim 11 wherein R1 is methyl and R2 is —NH—CO-(lower alkyl).

13. The method of claim 12 wherein R1 is methyl and R2 is —NH—CO—CH₃ or —NH—CO—CH₂—CH₂—CH₃.

14. A method of treating an inflammatory disease in an individual, comprising administering to the individual a composition comprising a therapeutically effective amount of an allocolchinone which inhibits microtubule assembly.

15. The method of claim 14 wherein the disease is selected from the group consisting of gout, Mediterranean fever, rheumatoid arthritis and osteoarthritis.

16. The method of claim 15 wherein the allocolchinone is represented by the following structure:

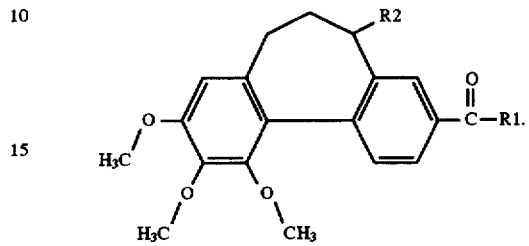

17. The method of claim 16 wherein R1 is methyl and R2 is —NH—CO-(lower alkyl).

18. The method of claim 17 wherein R1 is methyl and R2 is —NH—CO—CH₃ or —NH—CO—CH₂—CH₂—CH₃.

19. A method of inhibiting mitotic division in an individual, comprising administering to the individual an anti-mitotic amount of a composition comprising an allocolchinone which inhibits microtubule assembly.

20. The method of claim 19 wherein the allocolchinone is represented by the following structure:

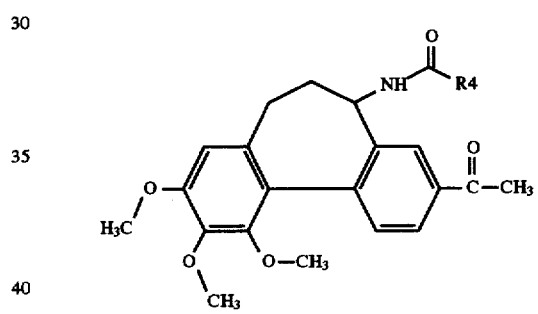

wherein R4 is methyl or propyl.

21. A method of treating an individual with a disease selected from the group consisting of multiple sclerosis, primary biliary cirrhosis, Alzheimer's Disease and Behcet's Disease, comprising administering to the individual a composition comprising a therapeutically effective amount of an allocolchinone which inhibits microtubule assembly.

22. The method of claim 21 wherein the allocolchinone is represented by the following structure:

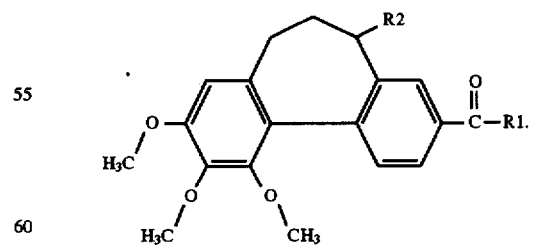

23. The method of claim 22 wherein R1 is methyl and R2 is —NH—CO-(lower alkyl).

24. The method of claim 23 wherein R1 is methyl and R2 is —NH—CO—CH₃ or —NH—CO—CH₂—CH₂—CH₃.

* * * * *